United States Patent
Donahoe et al.

(10) Patent No.: US 8,328,856 B1
(45) Date of Patent: *Dec. 11, 2012

(54) SURGICAL FIXATION SYSTEM AND RELATED METHODS

(75) Inventors: Ryan Donahoe, San Diego, CA (US); Andrew Schifle, San Diego, CA (US); Michael Barela, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 443 days.

This patent is subject to a terminal disclaimer.

(21) Appl. No.: 12/579,397

(22) Filed: Oct. 14, 2009

Related U.S. Application Data

(60) Provisional application No. 61/105,415, filed on Oct. 14, 2008.

(51) Int. Cl.
*A61B 17/80* (2006.01)
(52) U.S. Cl. .................. 606/294; 606/290; 606/293
(58) Field of Classification Search .................. 606/289, 606/290, 293, 295, 296
See application file for complete search history.

(56) References Cited

U.S. PATENT DOCUMENTS

| | | | |
|---|---|---|---|
| 4,143,883 A | 3/1979 | Paynter |
| 4,655,462 A | 4/1987 | Balsells |
| 4,794,918 A | 1/1989 | Wolter |
| 5,364,399 A | 11/1994 | Lowery |
| 5,549,607 A | 8/1996 | Olson |
| 5,549,612 A | 8/1996 | Yapp |
| 5,675,666 A | 10/1997 | Komuro |
| 5,876,402 A | 3/1999 | Errico |
| 5,931,838 A | 8/1999 | Vito |
| 5,951,558 A | 9/1999 | Fiz |
| 6,139,550 A | 10/2000 | Michelson |
| 6,152,927 A | 11/2000 | Farris |
| 6,193,721 B1 | 2/2001 | Michelson |
| 6,224,602 B1 | 5/2001 | Hayes |
| 6,235,033 B1 | 5/2001 | Brace |
| 6,235,034 B1 | 5/2001 | Bray |
| 6,241,731 B1 | 6/2001 | Fiz |
| 6,261,291 B1 | 7/2001 | Talaber |
| 6,290,703 B1 | 9/2001 | Ganem |
| 6,306,139 B1 | 10/2001 | Fuentes |
| 6,328,738 B1 | 12/2001 | Suddably |
| 6,331,179 B1 | 12/2001 | Freid |
| 6,361,537 B1 | 3/2002 | Anderson |
| 6,383,186 B1 | 5/2002 | Michelson |
| 6,398,783 B1 | 6/2002 | Michelson |
| 6,413,259 B1 | 7/2002 | Lyons |
| 6,416,528 B1 | 7/2002 | Michelson |
| 6,428,542 B1 | 8/2002 | Michelson |
| 6,454,771 B1 | 9/2002 | Michelson |

(Continued)

FOREIGN PATENT DOCUMENTS

WO 9851226 A 11/1998

(Continued)

OTHER PUBLICATIONS

PCT/US2008/009964, International Search Report. Nov. 7, 2008.

*Primary Examiner* — Andrew Yang
(74) *Attorney, Agent, or Firm* — NuVasive, Inc.; Jonathan Sprangler; Jennifer Russell

(57) ABSTRACT

A surgical fixation system having an improved mechanism to prevent the back out of screws employed in securing a surgical fixation plate to an intended orthopedic location.

13 Claims, 33 Drawing Sheets

U.S. PATENT DOCUMENTS

| | | |
|---|---|---|
| 6,458,133 B1 | 10/2002 | Lin |
| 6,503,250 B2 | 1/2003 | Paul |
| 6,527,776 B1 | 3/2003 | Michelson |
| 6,533,786 B1 | 3/2003 | Needham |
| 6,575,975 B2 | 6/2003 | Brace |
| 6,592,586 B1 | 7/2003 | Michelson |
| 6,595,993 B2 | 7/2003 | Donno |
| 6,599,290 B2 | 7/2003 | Bailey |
| 6,602,255 B1 | 8/2003 | Campbell |
| 6,620,163 B1 | 9/2003 | Michelson |
| 6,641,583 B2 | 11/2003 | Shluzas |
| 6,652,525 B1 | 11/2003 | Assaker |
| 6,669,700 B1 | 12/2003 | Farris |
| 6,695,846 B2 | 2/2004 | Richelsoph |
| 6,712,818 B1 | 3/2004 | Michelson |
| 6,730,127 B2 | 5/2004 | Michelson |
| 6,755,833 B1 | 6/2004 | Paul |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 6,945,973 B2 | 9/2005 | Bray |
| 6,969,390 B2 | 11/2005 | Michelson |
| 7,004,944 B2 | 2/2006 | Gause |
| 7,048,739 B2 | 5/2006 | Konieczynski |
| 7,060,067 B2 | 6/2006 | Needham |
| 7,074,221 B2 | 7/2006 | Michelson |
| 7,077,844 B2 | 7/2006 | Michelson |
| 7,087,057 B2 | 8/2006 | Konieczynski |
| 7,137,984 B2 | 11/2006 | Michelson |
| 7,220,263 B2 | 5/2007 | Cordaro |
| 2001/0047172 A1 | 11/2001 | Foley |
| 2002/0120273 A1 | 8/2002 | Needham |
| 2003/0078583 A1 | 4/2003 | Biedermann |
| 2003/0187440 A1 | 10/2003 | Richelsoph |
| 2004/0087951 A1 | 5/2004 | Khalili |
| 2004/0127897 A1 | 7/2004 | Freid |
| 2004/0127900 A1 | 7/2004 | Konieczynski |
| 2004/0153069 A1 | 8/2004 | Paul |
| 2004/0210217 A1 | 10/2004 | Baynham |
| 2004/0220572 A1 | 11/2004 | Michelson |
| 2004/0236334 A1 | 11/2004 | Michelson |
| 2004/0236335 A1 | 11/2004 | Michelson |
| 2005/0027293 A1 | 2/2005 | LeHuec |
| 2005/0033294 A1 | 2/2005 | Garden |
| 2005/0033298 A1 | 2/2005 | Hawkes |
| 2005/0038436 A1 | 2/2005 | Michelson |
| 2005/0049593 A1 | 3/2005 | Duong |
| 2005/0059971 A1 | 3/2005 | Michelson |
| 2005/0096657 A1 | 5/2005 | Autericque |
| 2005/0187552 A1 | 8/2005 | Michelson |
| 2005/0273105 A1 | 12/2005 | Konieczynski |
| 2005/0283152 A1 | 12/2005 | Lindemann |
| 2006/0100626 A1 | 5/2006 | Rathbun |
| 2006/0161157 A1 | 7/2006 | Mosca |
| 2006/0200147 A1 | 9/2006 | Ensign |
| 2007/0093832 A1 | 4/2007 | Abdelgany |

FOREIGN PATENT DOCUMENTS

| | | |
|---|---|---|
| WO | 0222030 A | 3/2002 |
| WO | 02080789 A | 10/2002 |

SURGICAL FIXATION SYSTEM AND RELATED METHODS

CROSS-REFERENCES TO RELATED APPLICATIONS

The present application is a non-provisional application claiming the benefit of priority under 35 USC §119(e) from U.S. Provisional Patent Application No. 61/105,415, filed Oct. 14, 2008, the entire contents of which are incorporated by reference into this disclosure.

BACKGROUND OF THE INVENTION

I. Field of the Invention

The present invention relates generally to the area of surgical fixation, and more particularly to a surgical fixation system having an improved mechanism to prevent the back out of screws employed in securing a surgical fixation plate to an intended orthopedic location.

II. Discussion of the Prior Art

The use of surgical fixation systems involving plates is accepted practice for a variety of orthopedic procedures. One procedure experiencing proliferated growth is that of spinal fusion, wherein a surgical fixation plate is secured along two or more vertebral bodies through the use of screws or fasteners extending through bores formed in the plate. Secured in this fashion, the surgical fixation plates serve to immobilize the vertebral bodies. When employed with bone allograft or another fusion-effecting implant (such as a mesh cage, a threaded cage, etc. . . . ), this immobilization promotes fusion to occur between the adjacent vertebral bodies, which is intended to restore disk height between the vertebral bodies and reduce pain in the patient.

A challenge exists in the use of spinal fixation plates, however, in that the screws employed to fix the spinal fixation plate to the vertebral bodies have a tendency to back out from the plate over time. One application where this is particularly worrisome is with the use of a spinal fixation plate positioned over the anterior cervical spine. More specifically, such backing out may cause the screws to come into unwanted contact with the esophagus, which may lead to damage or impairment to that organ. Another problem is that, with the screws backed out (partially or fully), the mechanical properties of the overall construct will become compromised, which may lead to a loss in the height of the intervertebral space height and thereby cause pain to the patient.

Another challenge involving cervical plates in particular exists in that it is desirable for a cervical plate to have minimal interference with the esophagus on the anterior side of the plate while having maximum surface area interaction with the vertebra on the posterior side of the plate. Many cervical plates in the prior art have a uniform thickness throughout, and to the extent that the surfaces of the plate are curved, this curvature is intended to facilitate the interaction with the vertebrae, often at the expense of the esophagus (in the form of discomfort to the patient).

The present invention is directed at overcoming, or at least reducing the effects of, one or more of the problems set forth above.

SUMMARY OF THE INVENTION

According to one broad aspect of the present invention, the present invention accomplishes this goal by providing a surgical fixation system including a plate, a plurality of screw members, and a corresponding number of anti-backout elements. According to one aspect of the present invention, the screws are prevented from backing out of the target site after placement through the use of the anti-backout elements in cooperation with recesses formed within the plate.

The plate includes a first surface, a second surface, and a plurality of bone screw apertures extending between the first and second surfaces. Each bone screw aperture has a first opening, a second opening, and an interior channel extending therebetween. A recess is provided within each bone screw aperture and is disposed circumferentially about the interior channel between the first and second openings. This recess is dimensioned to receive at least a portion of the anti-backout element.

The anti-backout element is provided as a generally circular canted coil ring member dimensioned to be received within the recess of the plate. The anti-backout element may be defined as having an outer circumference, an inner circumference and an aperture bounded by the inner circumference. Due to the canted coil nature of the anti-backout element, each of the circumferences is independently variable. For example, when inserted into the recess of the plate, the outer circumference may correspond to the rigid circumference of the recess. Upon insertion of a bone screw through the aperture, the inner circumference may expand to accommodate passage of a head portion of the bone screw. This expansion of the inner circumference occurs independently from the outer circumference (unlike would occur a solid snap ring, for example), and thus may occur without any expansion of the outer circumference, which is prevented from expanding by the limits of the recess. This independent expansion of the inner circumference occurs due to the canted nature of the coils in that the individual coils forming the anti-backout element will in effect be forced closer together by the screw head. In other words, the force exerted by the screw head does not cause purely radial expansion of the anti-backout element, but rather the canted nature of the coils allow the individual coils to be generally "flattened" against adjacent coils, in that the inner edges of the coils (forming the inner circumference) will tend to move in one direction, thus expanding the inner circumference, while the outer edges of the coils (forming the outer circumference) will remain stationary, causing no change in the outer circumference.

Each bone screw includes an anchor region, a head region, and a neck region. The anchor region includes a generally elongated shaft with at least one generally helical thread. Notably, the head region includes a lip portion having a diameter that is smaller than the first opening of the bone screw aperture, but greater than the second opening of the aperture. Thus, the lip portion will be able to pass through the first opening but not the second opening. The lip portion includes a generally planar ledge portion extending generally perpendicularly from the head region and a generally angled portion that connects the generally planar ledge portion to the neck region. Upon insertion of the screw into the aperture, the generally angled portion will apply a force to the anti-backout element, allowing passage of the ledge portion therethrough. Upon completion of insertion of the screw, the ledge portion is completely through the anti-backout element and interacts with the anti-backout element such that the ledge portion engages at least a portion of the inner circumference. The generally angled portion is prevented from passing through the second opening, and the ledge portion is prevented from passing through the anti-backout element (absent significant force which for example could be provided in a revision procedure using an appropriate tool). Thus, the anti-backout element interacts with the ledge portion to provide an anti-backout feature for the surgical fixation system.

According to a second broad aspect of the present invention, a surgical fixation system is provided adapted for dynamic anterior cervical fixation. This surgical fixation system comprises a surgical fixation plate assembly, a plurality of screws, a plurality of anti-backout elements, and a plurality of spring members. As will be explained in greater detail below, the surgical fixation system of the present invention may be used to provide temporary or permanent fixation along an orthopedic target site, including but not limited to adjacent vertebral levels within the spine (e.g. cervical spine during anterior fusion surgery, lumbar spine for anterior fusion surgery, etc. . . . ). To do so, the plate assembly is first positioned over the target site such that the screws and anti-backout elements may thereafter be employed to couple the plate to the target site. According to one aspect of the present invention, the screws are prevented from backing out of the target site after placement through the use of the anti-backout elements in cooperation with recesses formed within the plate.

The surgical fixation plate assembly includes a plurality of component plates that are slidably engageable relative to one another. Specifically, the plate assembly includes at least one interior plate flanked on either side by an end plate. When assembled, the surgical fixation plate assembly is an elongated construct having a longitudinal axis extending therethrough.

The interior plate includes a main body portion flanked by a pair of extensions, one extension positioned at a first longitudinal end, and the other extension positioned at a second longitudinal end. The main body portion includes a first surface, a second surface, and a plurality of bone screw apertures extending between the first and second surfaces. The first and second surfaces are generally curved in both longitudinal and lateral directions to help the plate assembly conform to the general shape of the cervical anatomy. The bone screw apertures are positioned in approximately the middle of interior plate on either side of the longitudinal midline. Each bone screw aperture has a first opening, a second opening, and an interior channel extending therebetween. A recess is provided within each bone screw aperture and is disposed circumferentially about interior channel between the first and second openings. This recess is dimensioned to receive at least a portion of the anti-backout element. The interior plate further includes a pair of viewing windows disposed along the longitudinal midline of the plate, on either side of the bone screw apertures. Viewing windows are provided to allow for visual location of the intervertebral space and/or fusion material.

The extensions are provided on longitudinal ends of the interior plate, and extend along substantially the lateral width of the interior plate. Each extension has a first edge comprising the junction between the extension and main body, a second edge opposite the first edge, and a pair of lateral edges extending between the first and second edges. Each extension further includes a first surface positioned on the same side of the interior plate as the first surface of the main body portion, and a second surface positioned on the same side of the interior plate as the second surface of the main body portion. Each extension is provided with a recess positioned proximate the second edges. The recess is an elongated recess having rounded ends, however any shape is possible. The recess is dimensioned to receive the spring member, as will be explained in greater detail below.

The spring member has an elongated configuration with a raised generally planar central portion flanked by a pair of generally convex portions positioned between the central portion and end portions. Spring member is formed from a resilient material (e.g. nitinol) such that it may be deformed without breaking and thereafter return to a normal configuration. The spring member serves a variety of purposes. As will be explained in greater detail below, the spring member prevents the interior plate from becoming detached from the end plates. Additionally, the spring member may be configured to exert a frictional force upon the end plates so as to provide a modicum of resistance over the translation of the plates relative to one another.

The spring member is configured to reside within the elongated recess of the interior plate. Upon placement in the recess, and without any other forces acting on the spring member (i.e. in a "natural" state), the spring member rests in the recess such that the end portions are contained within the recess and the central portion protrudes beyond the first surface of the extension. The recess and spring member are further sized and configured such that a downward force applied to the central portion of the spring member will cause the end portions to extend outward within the recess. This action causes the spring member to have a profile at least equal to, if not below, the first surface of the extension. This in turn will allow the interior plate and end plates to be mated, as will be explained in greater detail below.

The end plate includes a proximal end and a distal end. The proximal end is defined as the end in closest proximity to the interior plate upon assembly of the spinal fusion plate assembly. Correspondingly, the distal end is defined as the end in furthest proximity from the interior plate upon assembly of the spinal fusion plate assembly. The end plate further includes a first surface, a second surface, and a plurality of bone screw apertures extending between the first and second surfaces. The first and second surfaces are generally curved in both longitudinal and lateral directions to help the plate assembly conform to the general shape of the cervical anatomy. The bone screw apertures are positioned near the distal end of the end plate on either side of the longitudinal midline. Each bone screw aperture has a first opening, a second opening, and an interior channel extending therebetween. A recess is provided within each bone screw aperture and is disposed circumferentially about the interior channel between the first and second openings. This recess is dimensioned to receive at least a portion of the anti-backout element. The end plate further includes a viewing window disposed along the longitudinal midline of the plate, proximal of the bone screw apertures. Viewing window is provided to allow for visual location of the intervertebral space and/or fusion material.

The proximal end includes a hollow receiving area positioned between the first surface and second surface. The hollow receiving area includes a lower interior surface, and upper interior surface, and an opening. The hollow receiving area is sized and dimensioned to slidingly receive the entirety of extension of interior plate. The lower interior surface is dimensioned to interact with the second surface of the extension, and the upper interior surface is dimensioned to interact with the first surface of extension. The upper surface further includes an elongated recess positioned in the approximate middle thereof. The recess is dimensioned to receive the raised generally planar central portion and generally convex portions of the spring member 217 when the interior plate and end plate are coupled together. Specifically, the recess functions as a "track" for the spring member to migrate within while the end plate is translating relative to the interior plate. Furthermore, the end plate includes a wall portion positioned between the elongated recess and the opening that functions to block passage of the spring member and therefore prevent the end plate from uncoupling with the interior plate once assembled.

To assemble the construct, a spring member is placed within the recess on the extension of the interior plate. A downward force is applied to the spring member to urge the spring member fully into the recess. At this point the extension is inserted into a receiving area of an end plate via the opening. After the recess including the spring member is advanced beyond the wall portion of the end plate, the spring member returns to its "normal" positioning with the raised planar portion extending into recess of the hollow receiving are. Due to the inability of the spring member to pass beyond the wall portion, the interior plate and end plate are now effectively coupled together. The extension is free to bi-directionally translate within the hollow receiving area in the distal and proximal directions. The other end plate is added in the same manner to form the surgical fixation plate assembly.

According to another broad aspect of the present invention, a drill, tap, and screw (DTS) guide is provided that is configured to engage the surgical fixation systems disclosed above. The DTS guide includes an engagement assembly, an elongated body portion, and a handle member. The engagement assembly is located at a distal end of the elongated body portion, and the handle member extends from a proximal end of the elongated body portion. As will be explained in further detail below, the engagement assembly is operable to releasably grab and hold a portion of a bone fixation plate, for example a portion of the surgical fixation system described herein. The elongated body portion is sized and dimensioned to extend through an operative corridor to a surgical target site within a body. The handle member remains outside the body to enable operation of the DTS guide by a user.

In order to use the DTS guide, a surgeon grips the contoured handle with one hand and inserts the boss of the housing and flange of the actuator into first and second apertures, of the bone plate. At this point, the DTS guide is in a first position such that the flange and the boss are in a generally parallel orientation to one another, and the bone plate is not secured to the DTS guide. A space exists between the first housing portion and second housing portion of the actuator. The second pin is also positioned at a proximal end of the second aperture of the pivot member.

In order to operate the DTS guide, the surgeon rotates the thumbwheel in a clockwise direction. As the thumbwheel rotates, the inner shaft will also rotate in the same (clockwise) direction. Due to the interaction between the distal boss of the inner shaft and the proximal aperture of the connector, the connector also rotates in a clockwise direction. As the connector rotates, the interaction between the threaded portion of the connector and the threaded portion of outer tube (which is stationary) causes the connector to migrate distally within the outer tube. Because the distal boss of the inner shaft is slideably engaged with the proximal aperture of the connector, the distal boss continues to apply the appropriate torque to turn the connector. Since the connector is connected to the second housing portion of the actuator via the connecting flange, the distal migration of the connector causes likewise distal migration of the second housing portion until the gap is closed. This distal migration of the second housing portion causes a distal migration of the second pin within the second aperture. Due to the angled orientation of the second aperture, distal migration of the second pin therein causes the pivot member to pivot around the first pin. This pivoting movement causes the flange to migrate toward the boss such that the flange and boss exert a compressive force on the bone plate. This is the second, actuated position of the DTS guide.

To release the plate from the DTS guide, a surgeon rotates thumbwheel counter-clockwise until flange returns to the first position. Then, the surgeon pulls upward to release the boss and flange from the apertures of the bone plate.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The surgical fixation plate disclosed herein boasts a variety of inventive features and components that warrant patent protection, both individually and in combination.

This invention improves upon the prior art by providing a surgical fixation system including a surgical fixation plate, a plurality of screws, and a plurality of anti-backout elements, wherein the anti-backout elements are configured and dimensioned to be received within bone screw apertures formed in the surgical fixation plate to prevent the screws from backing out over time. As will be described below, the anti-backout elements are capable of being easily introduced into the bone screw apertures prior to introduction of the screws into a given orthopedic target. Although particularly suited for use in anterior cervical spine fixation, it will be readily appreciated by those skilled in the art that the surgical fixation system of the present invention may be employed in any number of suitable orthopedic fixation approaches and procedures, including but not limited to anterior, posterior, lateral, antero-lateral, postero-lateral, lumbar spine fixation, thoracic spine fixation, as well as any non-spine fixation application such as bone fracture treatment. Furthermore, although shown and described by way of example only as used in a 4-hole, twolevel plate, it will be appreciated that such an anti-backout feature may be employed in a plate having any number of bone screw apertures for fusion of any number of vertebral levels.

Figure 1:
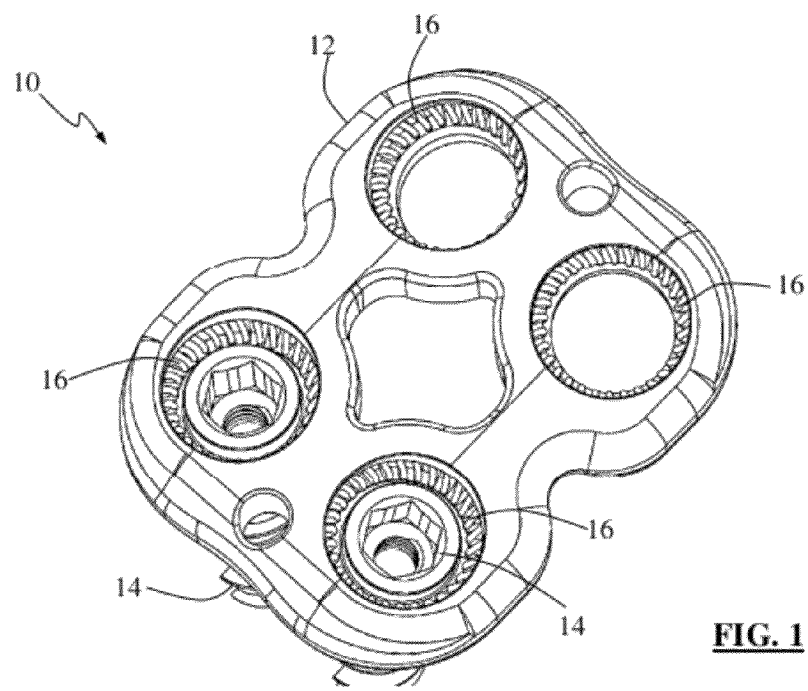
FIG. 1 is a perspective view of one example of a surgical fixation system 10 according to one embodiment of the present invention.
Figure 2:
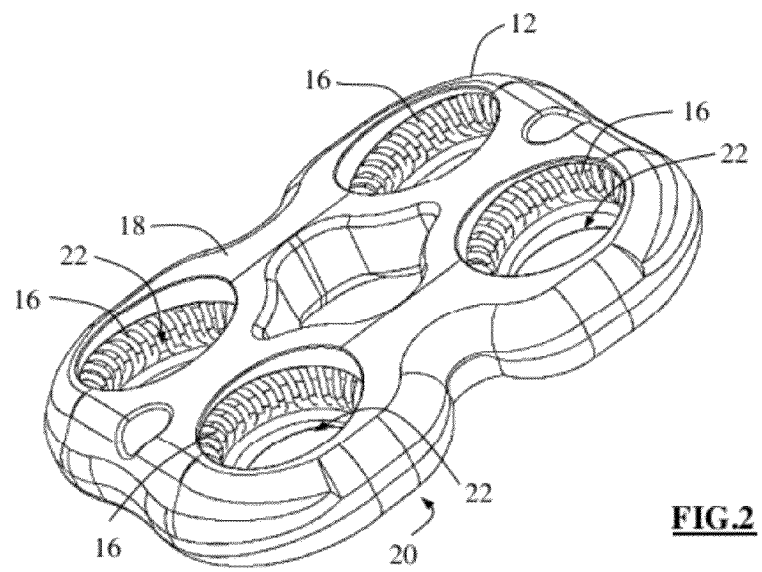
FIG. 2 is a perspective view of a bone plate provided with anti-backout elements forming part of the surgical fixation system of FIG. 1.

FIG. 1 illustrates an example of a surgical fixation system 10 according to a first embodiment of the present invention. Surgical fixation system 10 is similar to that shown and described in PCT Application Serial No. PCT/US08/09964, filed on Aug. 20, 2008 and entitled "Surgical Fixation System and Related Methods," the entire contents of which are hereby incorporated by reference as if set forth fully herein (attached hereto as Appendix A). The surgical fixation system 10 comprises a surgical fixation plate 12, a plurality of screws 14, and a plurality of anti-backout elements 16. As will be explained in greater detail below, the surgical fixation system 10 of the present invention may be used to provide temporary or permanent fixation along an orthopedic target site, including but not limited to adjacent vertebral levels within the spine (e.g. cervical spine during anterior fusion surgery, lumbar spine for anterior fusion surgery, etc. . . . ). To do so, the plate 12 is first positioned over the target site such that the screws 14 and anti-backout elements 16 may thereafter be employed to couple the plate 12 to the target site. According to one aspect of the present invention, the screws 14 are prevented from backing out of the target site after placement through the use of the anti-backout elements 16 in cooperation with recesses formed within the plate 12.

Referring to FIGS. 2-5, the surgical fixation plate 12 includes a first surface 18, a second surface 20, and a plurality of bone screw apertures 22 extending between the first and second surfaces 18, 20. Each bone screw aperture 22 has a first opening 24, a second opening 26, and an interior channel 28 extending therebetween. A recess 30 is provided within each bone screw aperture 22 and is disposed circumferentially about interior channel 28 between the first and second openings 24, 26. This recess is dimensioned to receive at least a portion of the anti-backout element 16.

Figure 3:
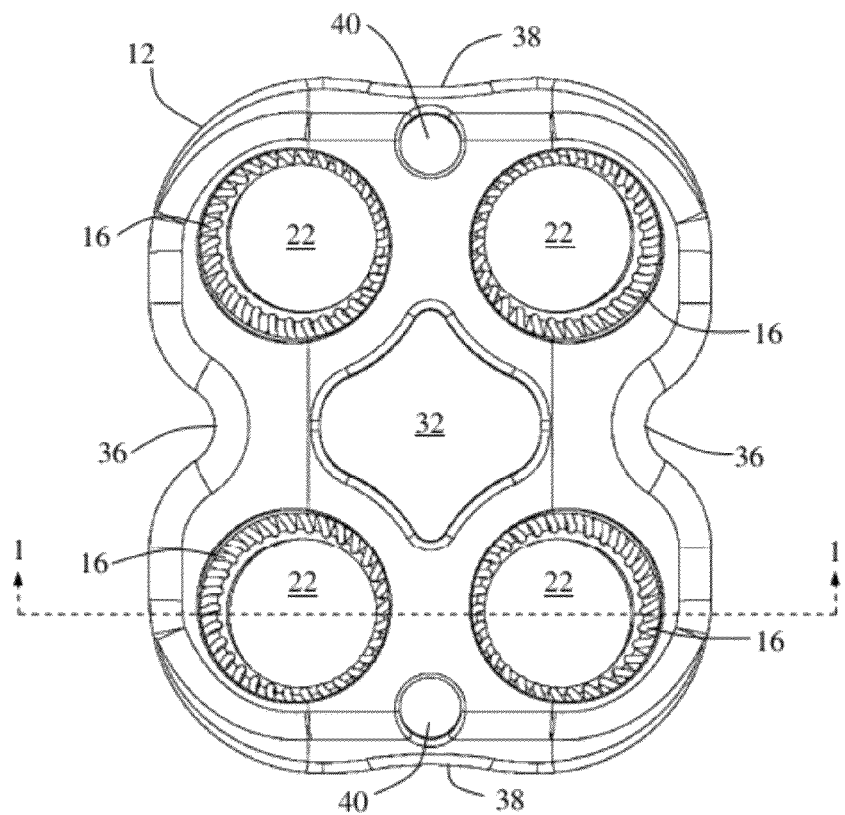
FIG. 3 is a top plan view of the bone plate of FIG. 2.
Figure 4:
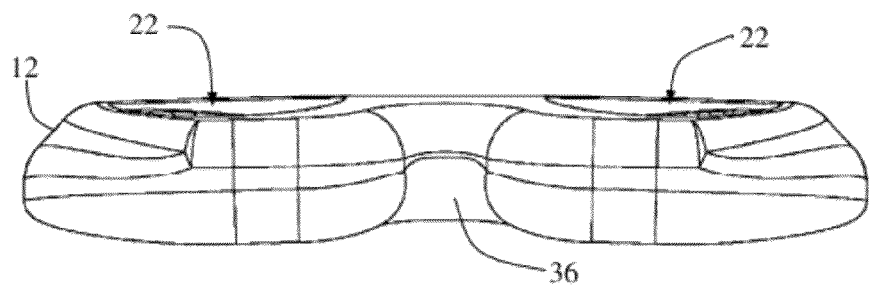
FIG. 4 is a side view of the bone plate of FIG. 2.
Figure 5:
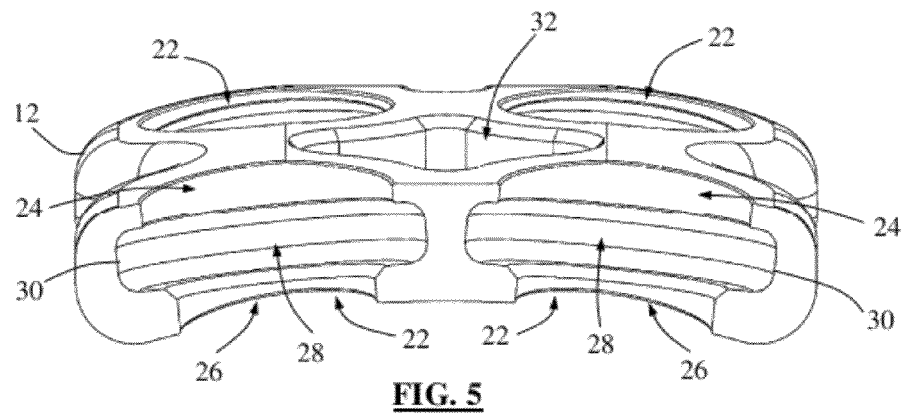
FIG. 5 is a partial cross-section view of the bone plate of FIG. 3 without the anti-backout elements, taken along line 1-1 of FIG. 3.

The plate 12 may be provided having any number of different peripheral profiles, including but not limited to the generally rectangular peripheral profile set forth by way of example in the figures (and best viewed in FIG. 3). The plate 12 may also be provided with or without viewing aperture 32 formed between the first and second surfaces 18, 20 and positioned generally in the central portion of plate 12. The viewing aperture 32 functions to provide the ability to see or visualize the spinal target site after the plate 12 has been secured to the patient. It will be appreciated that the viewing aperture 34 may be provided in any number of suitable shapes or configurations without departing from the scope of the invention, and therefore is not limited to the shape shown by way of example in FIG. 3.

In addition to the viewing apertures 32, the plate 12 may be configured to include indentations 36 positioned along the lateral sides of plate 12 in between each pair of adjacent apertures 22 as well as indentations 38 positioned on either end of the plate 12 in between each pair of adjacent apertures 22. The indentations 36, 38 reduce the amount of material used in manufacturing the plate 12, and reduce the overall profile of the plate 12 to augment the viewing capability already offered by the viewing aperture 32. At least one insertion aperture 40 may be provided at either end of the plate 12 for receiving at least a portion of an insertion instrument. By way of example only, the plate 12 shown in the attached figures includes a pair of insertion apertures 40, with one located at each end of the plate 12. The insertion apertures 40 are configured to engage at least a portion of an insertion device (not shown), and thus may include any suitable feature necessary to allow such engagement, including but not limited to threading, ridges, and recesses.

Figure 6:
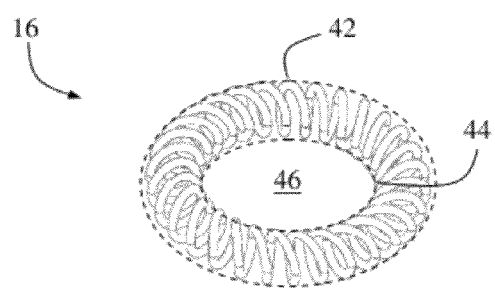
FIG. 6 is a perspective view of an anti-backout element forming part of the surgical fixation system of FIG. 1.
Figure 7:
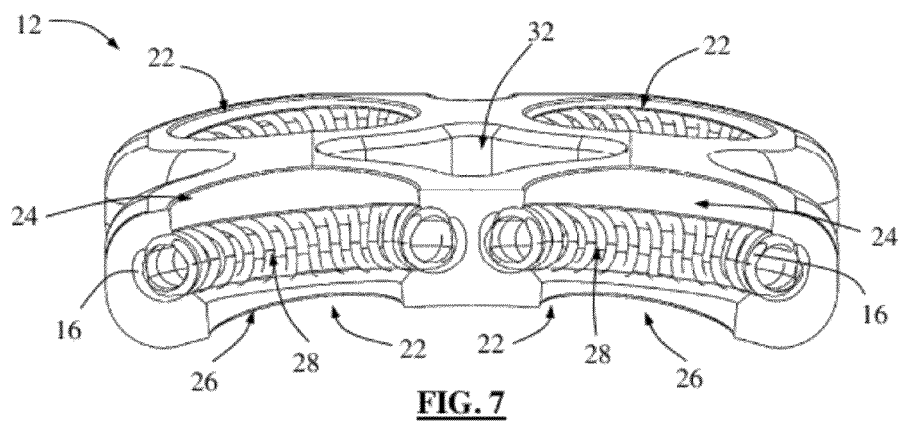
FIG. 7 is a partial cross-section view of the bone plate of FIG. 3 including the anti-backout elements, taken along line 1-1 of FIG. 3.

FIG. 6 illustrates one example of an anti-backout element 16 according to one embodiment of the present invention. By way of example only, anti-backout element 16 is generally provided as a generally circular (or annular), unbroken canted coil ring member dimensioned to be received within the recess 30 of plate 12. The anti-backout element 16 may be defined as having an outer circumference 42, an inner circumference 44 and an aperture 46 bounded by the inner circumference 44. Due to the canted coil nature of the anti-backout element 16, each of the circumferences 42, 44 are independently variable. For example, when inserted into the recess 30 of plate 12 (as shown in FIG. 7), the outer circumference 42 may correspond to the rigid circumference of the recess 30. Upon insertion of a bone screw through aperture 46, the inner circumference 44 may expand to accommodate passage of a head portion of the bone screw (described in further detail below). This expansion of the inner circumference 44 occurs independently from the outer circumference 42 (unlike would occur a solid snap ring, for example), and thus may occur without any expansion of the outer circumference 42, which is prevented from expanding by the limits of the recess 30. This independent expansion of the inner circumference 44 occurs due to the canted nature of the coils (illustrated in FIG. 6) in that the individual coils forming the anti-backout element 16 will in effect be forced closer together by the screw head. In other words, the force exerted by the screw head does not cause purely radial expansion of the anti-backout element 16, but rather the canted nature of the coils allow the individual coils to be generally "flattened" against adjacent coils, in that the inner edges of the coils (forming the inner circumference) will tend to move in one direction, thus expanding the inner circumference, while the outer edges of the coils (forming the outer circumference) will remain stationary, causing no change in the outer circumference.

By way of example only, the anti-backout element 16 may be have any number suitable sizes, both of the individual rings and of the outer and inner circumferences 42, 44. The anti-backout element 16 may be formed of any suitable biocompatible material, including but not limited to metal. According to a preferred embodiment, in use the anti-backout elements 16 are provided within recess 30 of plate 12 prior to insertion during the surgical procedure. It will be appreciated, however, that the anti-backout elements 16 may alternatively be positioned within a corresponding groove formed within the head of a screw without departing from the scope of the present invention.

Figure 8:
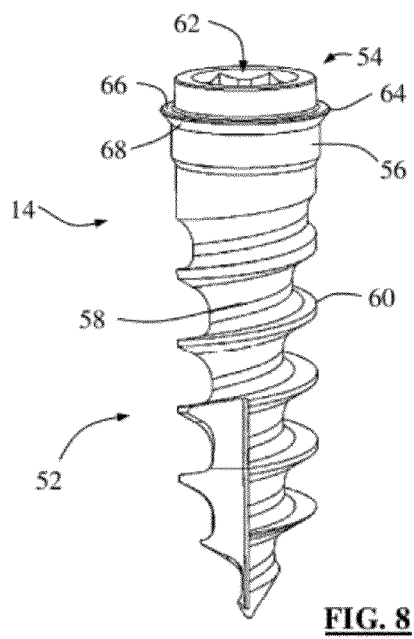
FIG. 8 is a perspective view of one example of a fixed-angle bone screw forming part of the surgical fixation system of FIG. 1.

FIG. 8 illustrates an example of a fixed-angle bone screw 14 according to one embodiment of the present invention. Each screw 14 includes an anchor region 52 and a head region 54 separated by a neck region 56. The anchor region 52 includes a generally elongated shaft 58 with at least one generally helical thread 60. The shaft 58 has a smaller diameter than the bone screw aperture 22, the neck region 56 and thread 60 have a substantially similar diameter to that of the aperture 22, and the head region 54 has an outer diameter greater than that of the aperture 22. Additionally, the neck region 56 is generally cylindrical in shape, which combined with the relative size to the aperture 22 prevents movement of fixed-angle screw 14 once inserted into aperture 22. As the bone screw 14 is advanced through plate 12, the thread 60 engages with the bone securing the plate 12 to the vertebra. The head region 54 may be equipped with any number of mechanisms for engagement with an introduction device (e.g. a screw driver), including but not limited to the hex-head recess 62. Moreover, although shown as a single thread 60, it will be appreciated that the elongated shaft 58 may be equipped with multiple threads 60 without departing from the scope of the present invention.

Figure 16:
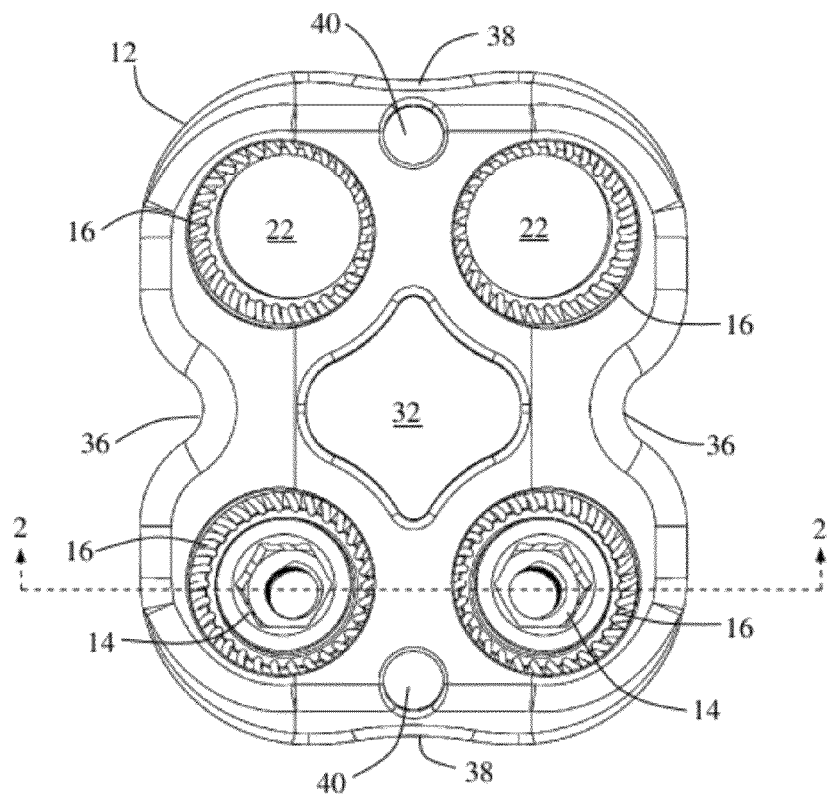
FIG. 16 is a top view of the surgical fixation system of FIG. 1.
Figure 17:
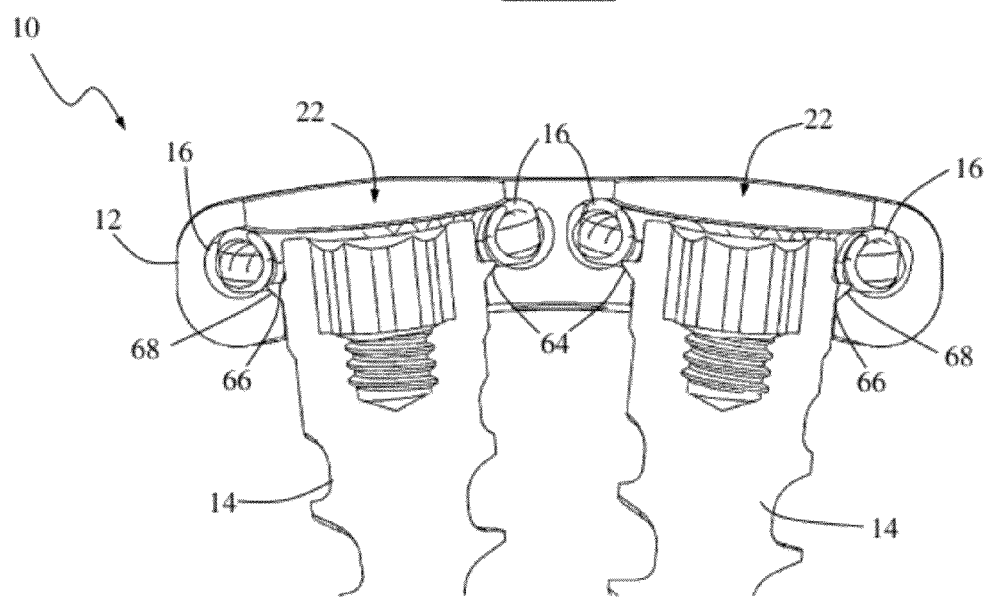
FIG. 17 is a partial cross-section view of the surgical fixation system of FIG. 16 taken along line 2-2 of FIG. 16.

Notably, the head region 54 includes a lip portion 64 having a diameter that is smaller than the first opening 24 of the aperture 22, but greater than the second opening 26 of the aperture 22. Thus, the lip portion 64 will be able to pass through the first opening 24 but not the second opening 26. Lip portion 64 includes a generally planar ledge portion 66 extending generally perpendicularly from the head region 54 and a generally angled portion 68 that connects the generally planar ledge portion 66 to the neck region 56. As shown in FIGS. 16-17, upon insertion of the screw 14 into the aperture 22, the generally angled portion 68 will apply a force to the anti-backout element 16 as described above, allowing passage of the ledge portion 66 therethrough. Upon completion of insertion of the screw 14, the ledge portion 66 is completely through the anti-backout element 16 and interacts with the anti-backout element 16 such that the ledge portion 66 engages at least a portion of the inner circumference 44. The generally angled portion 66 is prevented from passing through the second opening 26, and the ledge portion 66 is prevented from passing through the anti-backout element 16 (absent significant force which for example could be provided in a revision procedure using an appropriate tool). Thus, the anti-backout element 16 interacts with the ledge portion 66 to provide an anti-backout feature for the fixation system 10.

Figure 9:
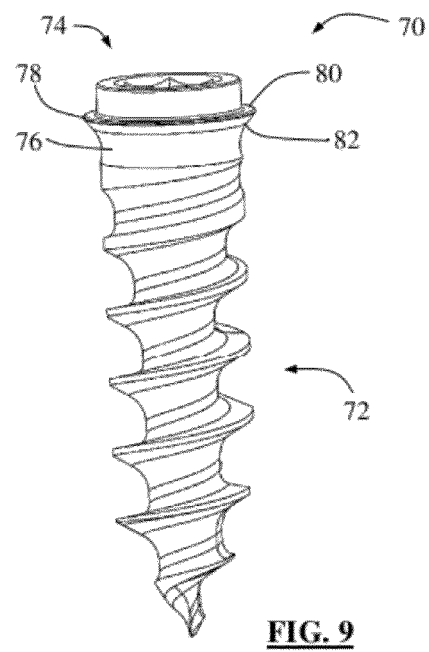
FIG. 9 is a perspective view of one example of a variable angle bone screw forming part of the surgical fixation system of FIG. 1.

FIG. 9 illustrates one example of a polyaxial bone screw 70 according to one embodiment of the present invention. Each screw 70 includes an anchor region 72 and a head region 74 separated by a neck region 76. The corresponding features are similar to those of the fixed-angle screw 14 such that a repetition is not necessary. The notable difference, however is that the neck region 76 is generally curved or tapered to allow for movement of the screw once inserted into the vertebra due to natural shifting of the vertebrae during normal activity of the patient. As with the fixed-angle screw 14 described above, the polyaxial bone screw 70 is provided with a lip portion 78 having a generally planar ledge portion 80 extending generally perpendicularly from the head region 74 and a generally angled portion 82 connecting the ledge portion 80 to the neck portion 76. Thus, the polyaxial bone screw 70 is provided with the same anti-backout feature of the fixed-angle screw 14. Similarly the head region 74 may be equipped with any number of mechanisms for engagement with an introduction device (e.g. a screw driver), including but not limited to the hex-head recess 75.

Figure 10:
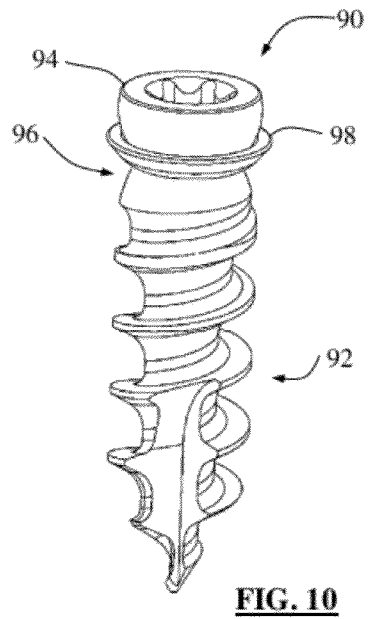
FIG. 10 is a perspective view of a second example of a variable angle bone screw forming part of the surgical fixation system of FIG. 1.
Figure 11:
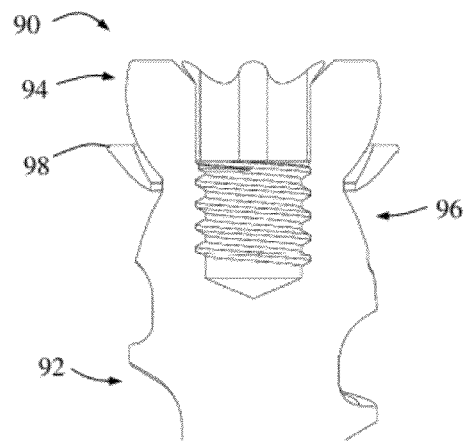
FIG. 11 is a partial cross-section of the bone screw of FIG. 10.
Figure 12:
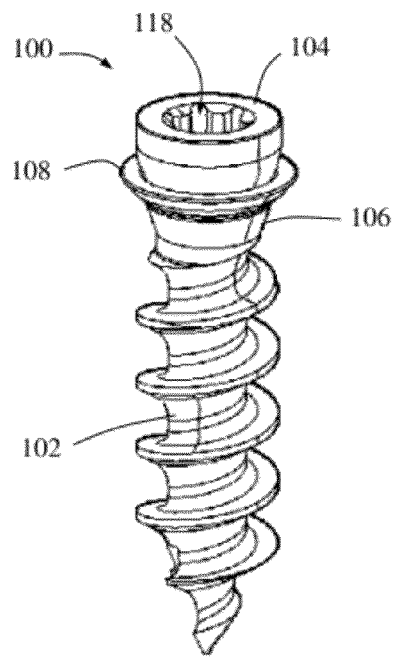
FIG. 12 is a perspective view of a third example of a variable angle bone screw forming part of the surgical fixation system of FIG. 1.
Figure 13:
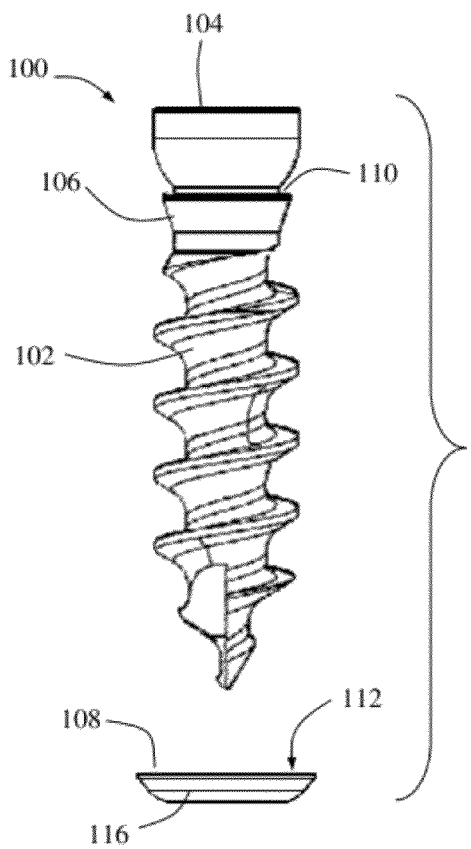
FIG. 13 is an exploded view of the variable angle bone screw of FIG. 12.
Figure 14:
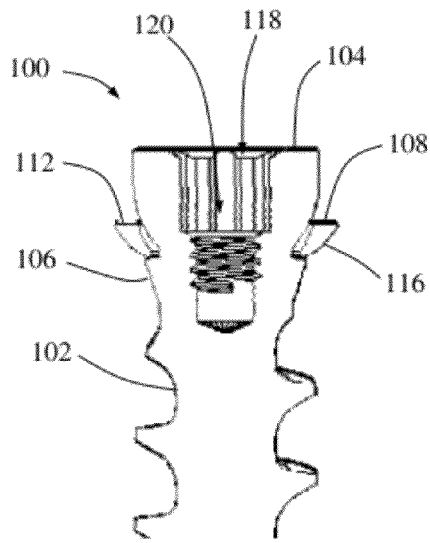
FIG. 14 is a partial cross-sectional view of the variable angle bone screw of FIG. 12.
Figure 15:
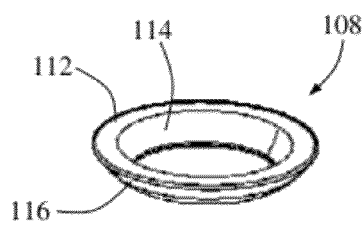
FIG. 15 is a perspective view of a lip member forming part of the variable angle bone screw of FIG. 12.

FIGS. 10-11 illustrate one example of a polyaxial bone screw 90 according to an alternative embodiment of the present invention. Screw 90 includes an anchor portion 92, a head portion 94, and a neck region 96 therebetween. Screw 90 differs from screw 70 in that the lip portion 98 is not an integral portion of the screw 90, and can therefore migrate within limit about the head portion 94. Thus, when inserted into the plate 12 at an angle, the lip portion 98 may move slightly to flushly engage the anti-backout element 16 and create a potentially easier insertion of the bone screw 90. Once inserted, the screw 90 has the same anti-backout features as described above. The head region 94 may be equipped with any number of mechanisms for engagement with an introduction device (e.g. a screw driver), including but not limited to the hex-head recess 95. Moreover, the head region 94 may further included an internal threaded region 97 for engagement with a removal device in the event of a revision or repositioning of the bone screw 90. This feature may be present on any embodiment of bone screw described herein without departing from the scope of the present invention.

FIGS. 12-15 illustrate another example of a polyaxial bone screw 100 according to a further alternative embodiment of the present invention. Screw 100 includes an anchor portion 102, a head portion 104, and a neck region 106 therebetween. Screw 100 is similar to screw 90 in that the lip portion 108 is not an integral portion of the screw 100, and can therefore migrate within limit about the head portion 104. Thus, when inserted into the plate 12 at an angle, the lip portion 108 may move slightly to flushly engage the anti-backout element 16 and create a potentially easier insertion of the bone screw 100. Once inserted, the screw 100 has the same anti-backout features as described above. The head portion 104 may be equipped with any number of mechanisms for engagement with an introduction device (e.g. a screw driver), including but not limited to the hex-head recess 118. Moreover, the head portion 104 may further included an internal threaded region 120 for engagement with a removal device in the event of a revision or repositioning of the bone screw 100.

Bone screw 100 differs from screw 90 in that the neck region 106 is angled outward and terminates in a generally planar shelf 110 at the base of the head portion 104. The shelf 110 serves to retain the lip portion 108 and prevent it from migrating distally along the anchor portion 102. Lip portion 108 is generally circular in shape and includes a top surface 112, interior circumferential surface 114, and lateral circumferential surface 116. Top surface 112 is generally flat and dimensioned to interface with the anti-backout element 16 as described above. Interior circumferential surface 114 is semi spherical in shape to match the semi-spherical shape of the base of the head portion 104. Lateral circumferential surface 116 extends in a generally curved manner from the edge of the top surface 112 until it interfaces with the interior circumferential surface 114.

To assemble bone screw 100, the lip portion 108 is threadedly advanced along the anchor portion 102 to the base of the neck region 106. The circumference of the bottom end of the lip portion 108 is smaller than the circumference of the shelf 110. However, the circumference of the bottom end of the lip portion 108 will expand slightly as the lip portion is advanced beyond the shelf 110, allowing a snap-fit assembly of the bone screw 100.

Figure 18:
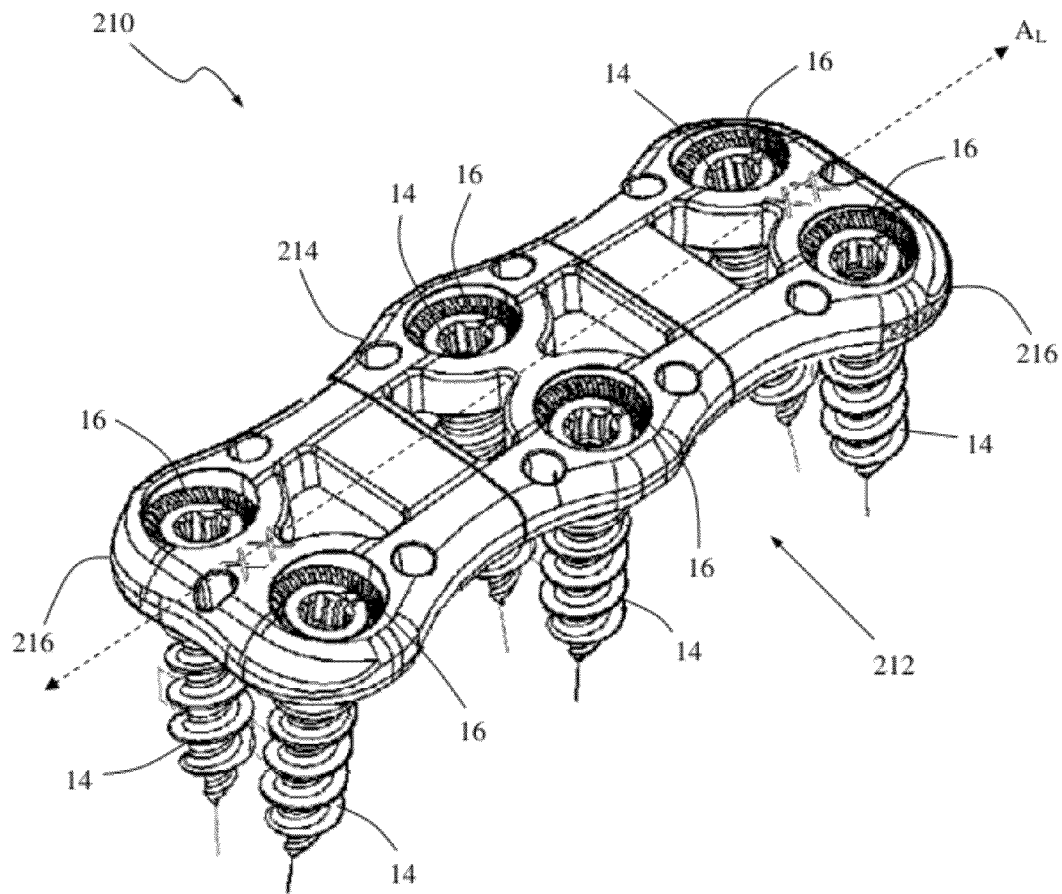
FIGS. 18-19 are perspective and exploded views, respectively, of an example of a surgical fixation system according to a second embodiment of the present invention, including a plate assembly and a plurality of fixation screws.
Figure 19:
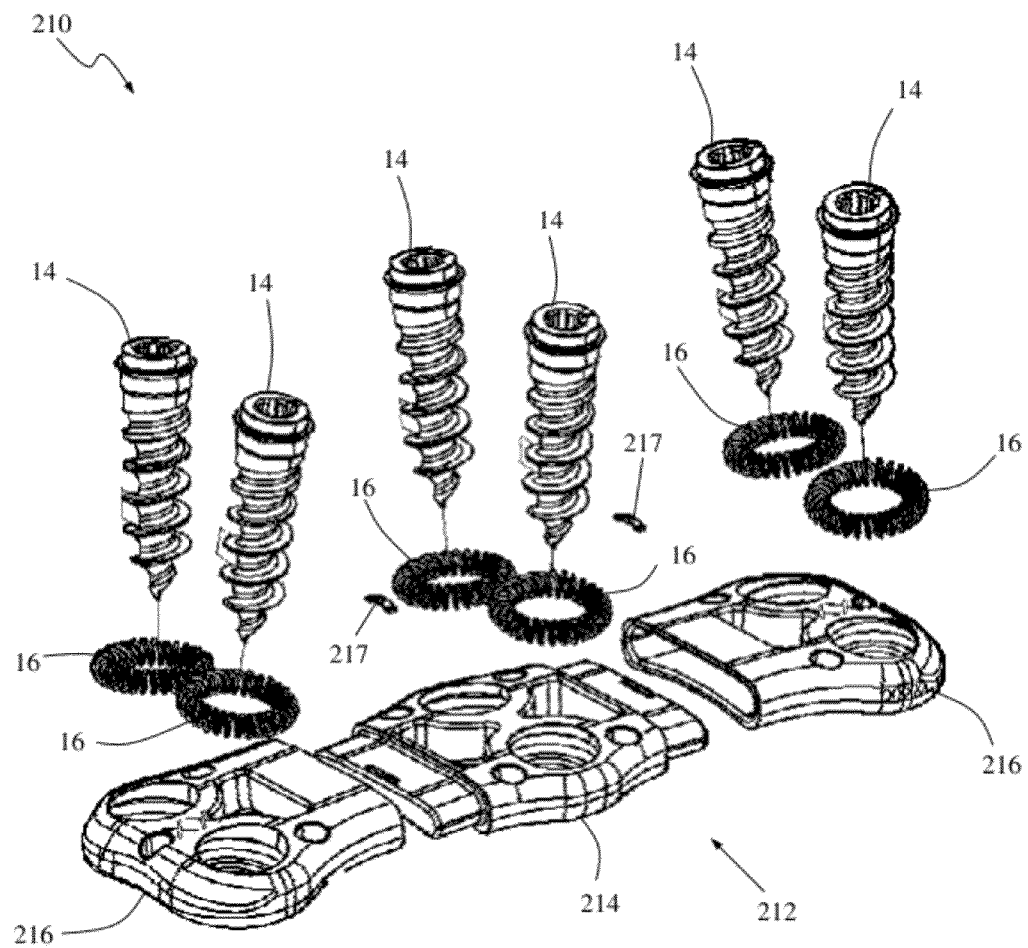
Figure 20:
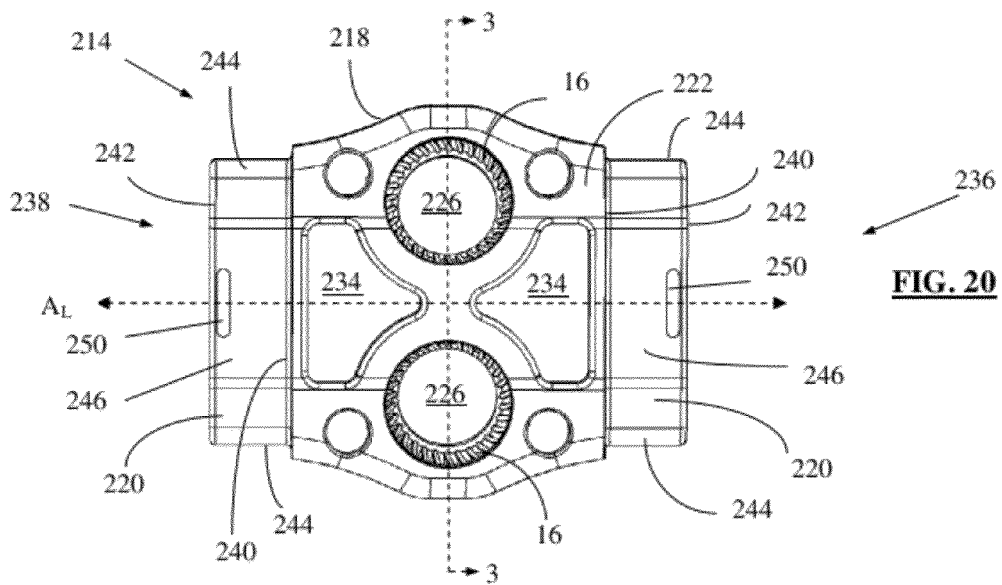
FIG. 20 is a top view of an interior plate member forming part of the plate assembly of FIG. 18.
Figure 21:
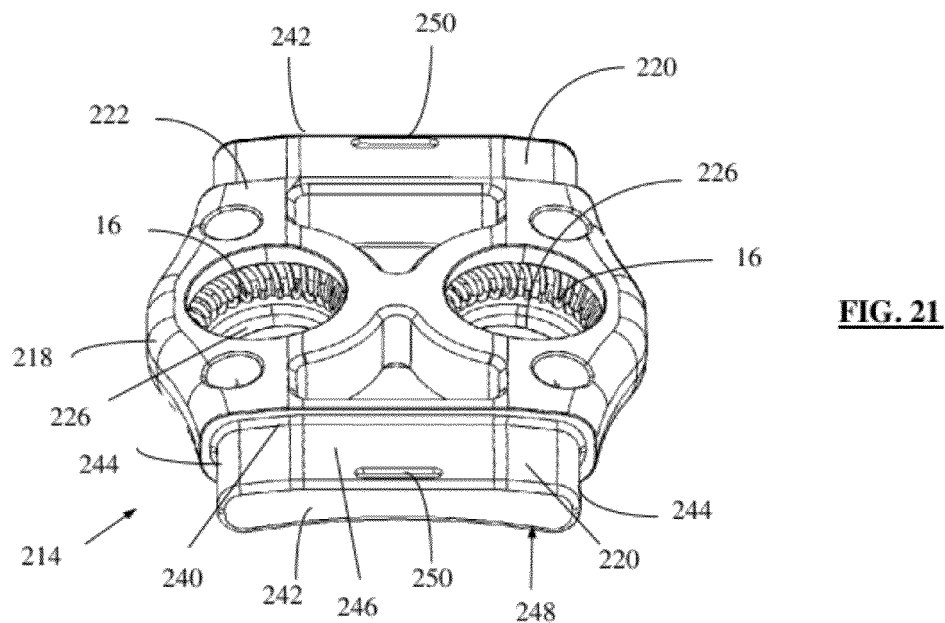
FIG. 21 is a perspective view of the interior plate member of FIG. 20.
Figure 22:
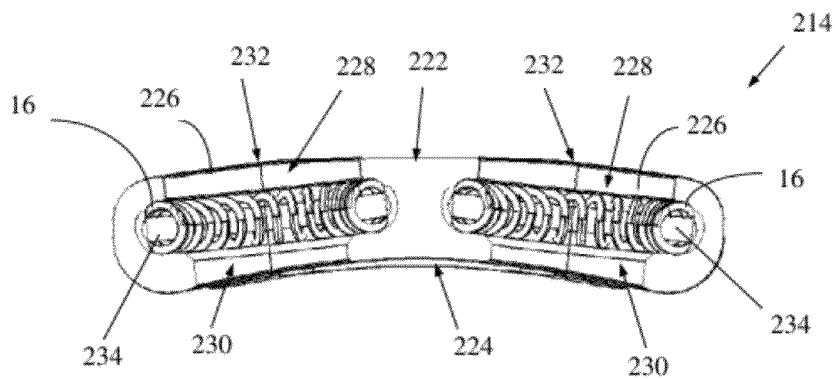
FIG. 22 is a partial cross-sectional view of the interior plate member of FIG. 20 including the anti-backout elements, taken along line 3-3 of FIG. 20.
Figure 23:
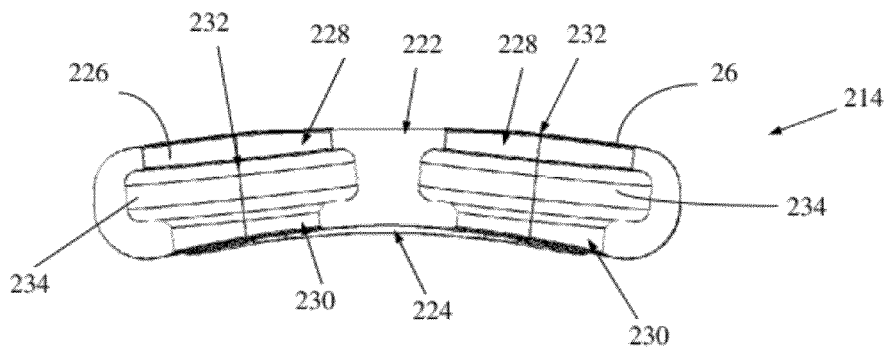
FIG. 23 is a partial cross-sectional view of the interior plate member of FIG. 20 without the anti-backout elements, taken along line 3-3 of FIG. 20.

FIGS. 18-19 illustrate a surgical fixation system 210 according to a second broad aspect of the present invention. For the simplicity of disclosure, elements of surgical fixation system 210 that are substantially identical to elements of surgical fixations system 10 have been assigned the same callout numbers. Surgical fixation system 210 represents an example of a specific embodiment of the present invention adapted for dynamic anterior cervical fixation. Surgical fixation system 210 comprises a surgical fixation plate assembly 212, a plurality of screws 14, a plurality of anti-backout elements 16, and a plurality of spring members 217. As will be explained in greater detail below, the surgical fixation system 210 of the present invention may be used to provide temporary or permanent fixation along an orthopedic target site, including but not limited to adjacent vertebral levels within the spine (e.g. cervical spine during anterior fusion surgery, lumbar spine for anterior fusion surgery, etc. . . . ). To do so, the plate assembly 212 is first positioned over the target site such that the screws 14 and anti-backout elements 16 may thereafter be employed to couple the plate 212 to the target site. According to one aspect of the present invention, the screws 14 are prevented from backing out of the target site after placement through the use of the anti-backout elements 16 in cooperation with recesses formed within the plate 212. It will be appreciated that the structure and function of the bone screws 14 and anti-backout elements 16 are identical as described above in relation to the plate 10, and therefore a discussion of such is not necessary to be repeated here.

The surgical fixation plate assembly 212 includes a plurality of component plates 214, 216, that are slidably engageable relative to one another. Specifically, the plate assembly 212 includes at least one interior plate 214 flanked on either side by an end plate 216. When assembled, the surgical fixation plate assembly 212 is an elongated construct having a longitudinal axis $A_L$ extending therethrough. End plates 216 are identical to one another, and so description of the construct will proceed with description of only one end plate 216 with the understanding that a pair of identical end plates 216 is used in conjunction with the present invention. Furthermore, the surgical fixation system 210 shown and described herein by way of example only is described in relation to a 2-level spine surgery (i.e. spanning two intervertebral disc spaces and three vertebral bodies). However, additional spinal levels may be addressed by including additional interior plates 214 without departing from the scope of the present invention.

FIGS. 20-23 illustrate an example of the interior plate 214 according to one embodiment of the present invention. The interior plate 214 includes a main body portion 218 flanked by a pair of extensions 220, one extension 220 positioned at a first longitudinal end 236, and the other extension 220 positioned at a second longitudinal end 238. The main body portion 218 includes a first surface 222, a second surface 224, and a plurality of bone screw apertures 226 extending between the first and second surfaces 222, 224. The first and second surfaces 222, 224 are generally curved in both longitudinal and lateral directions to help the plate assembly 212 conform to the general shape of the cervical anatomy. The bone screw apertures 226 are positioned in approximately the middle of interior plate 214 on either side of the longitudinal midline. Each bone screw aperture 226 has a first opening 228, a second opening 230, and an interior channel 232 extending therebetween. A recess 234 is provided within each bone screw aperture 226 and is disposed circumferentially about interior channel 232 between the first and second openings 228, 230. This recess is dimensioned to receive at least a portion of the anti-backout element 16. The interior plate 214 further includes a pair of viewing windows 234 disposed along the longitudinal midline of the plate, on either side of the bone screw apertures 226. Viewing windows are provided to allow for visual location of the intervertebral space and/or fusion material. By way of example only, the viewing apertures 234 are provided in the embodiment shown in FIG. 20 as having a curved chevron shape, however other shapes are possible, including but not limited to generally rectangular, generally ovoid, generally circular, and generally polygonal.

Extensions 220 are provided on longitudinal ends 236, 238 of the interior plate 214, and extend along substantially the lateral width of the interior plate 214. Each extension 220 has a first edge 240 comprising the junction between the extension 220 and main body 218, a second edge 242 opposite the first edge 240, and a pair of lateral edges 244 extending between the first and second edges 240, 242. Each extension 220 further includes a first surface 246 positioned on the same side of the interior plate 214 as the first surface 222 of the main body portion 218, and a second surface 248 positioned on the same side of the interior plate 214 as the second surface 224 of the main body portion 218. Each extension 220 is provided with a recess 250 positioned proximate the second edges 242. Recess 250 is an elongated recess having rounded ends, however any shape is possible. Recess 250 is dimensioned to receive the spring member 217, as will be explained in greater detail below.

Figure 24:
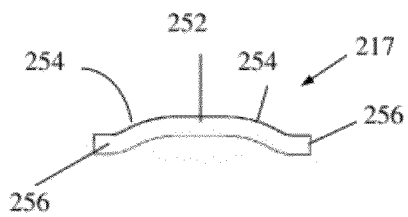
FIGS. 24-25 are plan and perspective views, respectively, of a spring member forming part of the surgical fixation system of FIG. 18.
Figure 25:
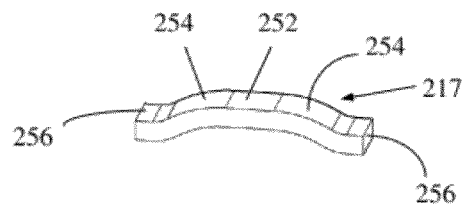

FIGS. 24-25 illustrate an example of a spring member 217 for use with the surgical fixation plate assembly 212 of the present invention. Spring member 217 has an elongated configuration with a raised generally planar central portion 252 flanked by a pair of generally convex portions 254 positioned between the central portion 252 and end portions 256. Spring member 217 is formed from a resilient material (e.g. nitinol) such that it may be deformed without breaking and thereafter return to a normal configuration. Spring member 217 serves a variety of purposes. As will be explained in greater detail below, the spring member 217 prevents the interior plate 214 from becoming detached from the end plates 216. Additionally, the spring member 217 may be configured to exert a frictional force upon the end plates 216 so as to provide a modicum of resistance over the translation of the plates relative to one another.

Figure 26:
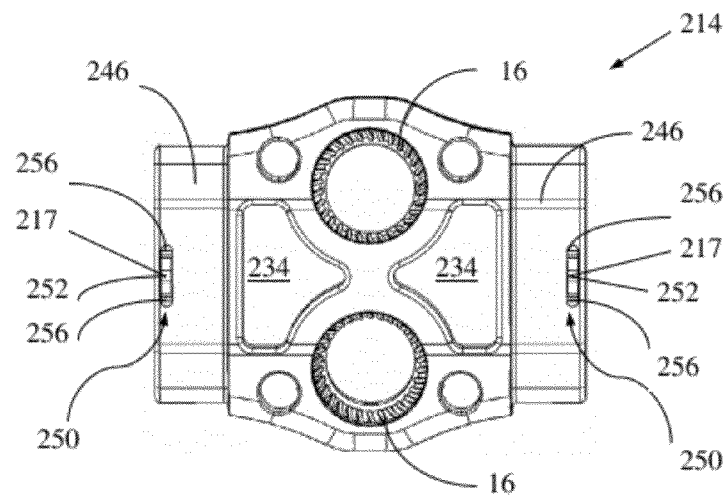
FIGS. 26-28 are top plan, perspective, and side plan views, respectively, of the spring member of FIG. 24 coupled with the interior plate member of FIG. 20.
Figure 27:
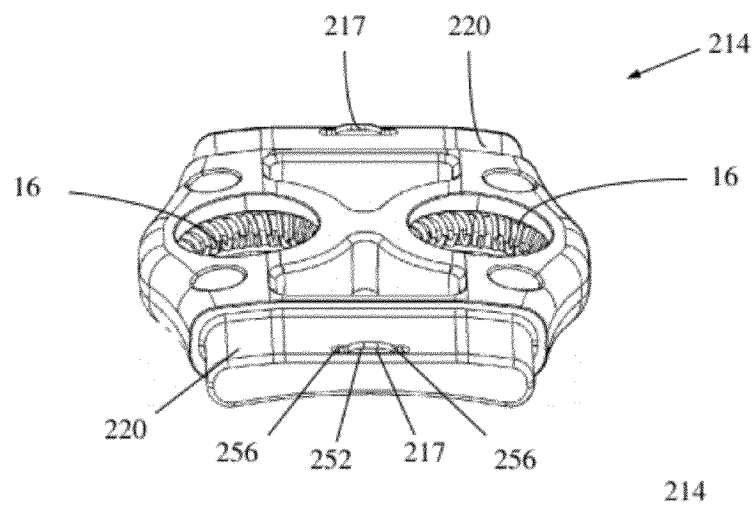
Figure 28:
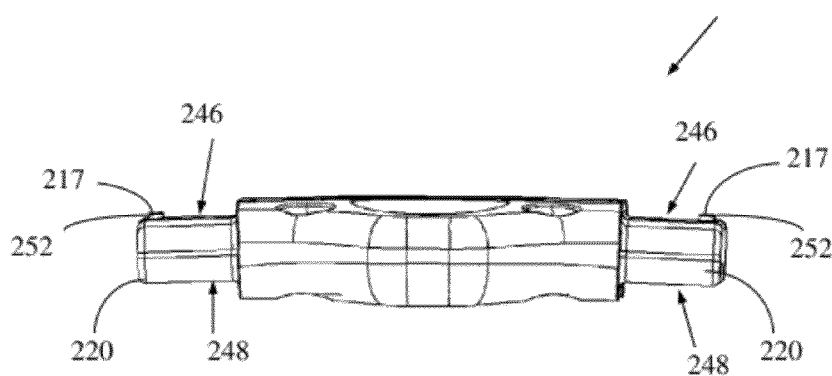
Figure 29:
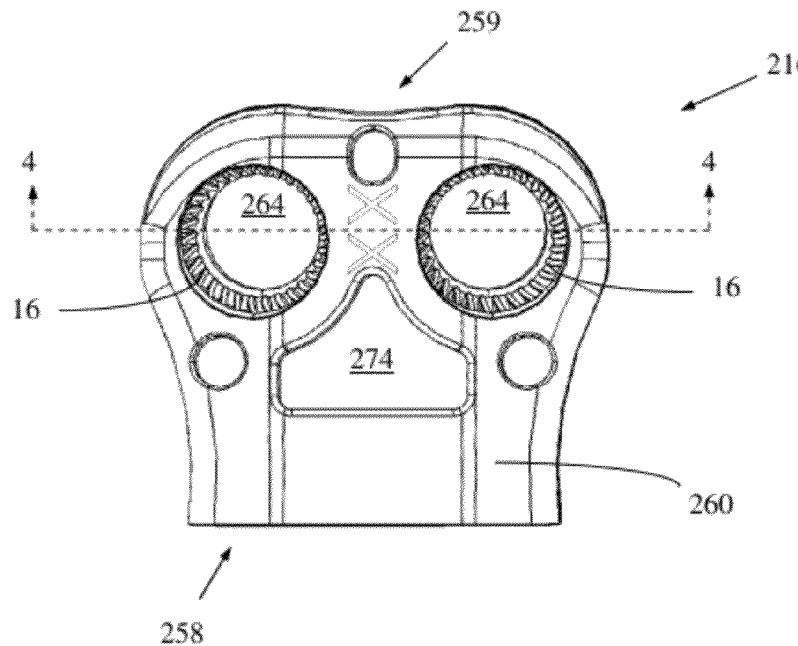
FIG. 29 is a top plan view of an end plate member forming part of the plate assembly of FIG. 18.
Figure 30:
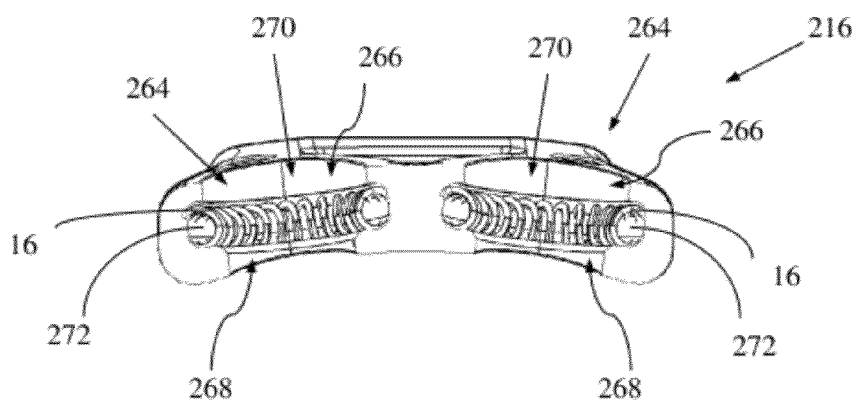
FIG. 30 is a partial cross-sectional view of the end plate member of FIG. 29 including the anti-backout elements, taken along line 4-4 of FIG. 29.
Figure 31:
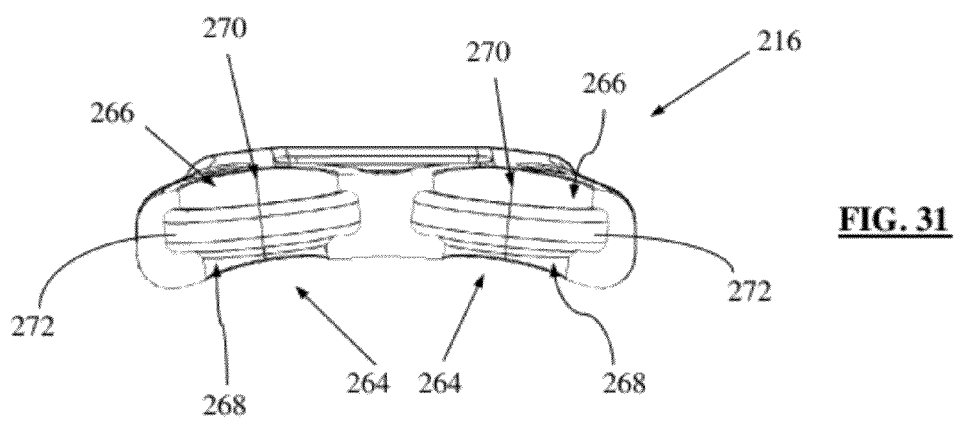
FIG. 31 is a partial cross-sectional view of the interior plate member of FIG. 29 without the anti-backout elements, taken along line 4-4 of FIG. 29.

Referring to FIGS. 26-28, the spring member 217 is configured to reside within the elongated recess 250 of the interior plate 214. Upon placement in the recess, and without any other forces acting on the spring member 217 (i.e. in a "natural" state), the spring member 217 rests in the recess 250 such that the end portions 256 are contained within the recess 250 and the central portion 252 protrudes beyond the first surface 246 of the extension 220. The recess 250 and spring member 217 are further sized and configured such that a downward force applied to the central portion 252 of the spring member 217 will cause the end portions 256 to extend outward within the recess 250. This action causes the spring member 217 to have a profile at least equal to, if not below, the first surface 246 of the extension 220. This in turn will allow the interior plate 214 and end plates 216 to be mated, as will be explained in greater detail below.

FIGS. 29-34 illustrate an example of an end plate 216 according to one embodiment of the present invention. The end plate 216 includes a proximal end 258 and a distal end 259. The proximal end 258 is defined as the end in closest proximity to the interior plate 214 upon assembly of the spinal fusion plate assembly 212. Correspondingly, the distal end 259 is defined as the end in furthest proximity from the interior plate 214 upon assembly of the spinal fusion plate assembly 212. The end plate 216 further includes a first surface 260, a second surface 262, and a plurality of bone screw apertures 264 extending between the first and second surfaces 260, 262. The first and second surfaces 260, 262 are generally curved in both longitudinal and lateral directions to help the plate assembly 212 conform to the general shape of the cervical anatomy.

The bone screw apertures 264 are positioned near the distal end 259 of end plate 216 on either side of the longitudinal midline. Each bone screw aperture 264 has a first opening 266, a second opening 268, and an interior channel 270 extending therebetween. A recess 272 is provided within each bone screw aperture 264 and is disposed circumferentially about interior channel 270 between the first and second openings 266, 268. This recess is dimensioned to receive at least a portion of the anti-backout element 16. The end plate 216 further includes a viewing window 274 disposed along the longitudinal midline of the plate, proximal of the bone screw apertures 226. Viewing window 274 is provided to allow for visual location of the intervertebral space and/or fusion material. By way of example only, the viewing aperture 274 is provided in the embodiment shown in FIG. 29 as having a curved chevron shape, however other shapes are possible, including but not limited to generally rectangular, generally ovoid, generally circular, and generally polygonal.

Figure 32:
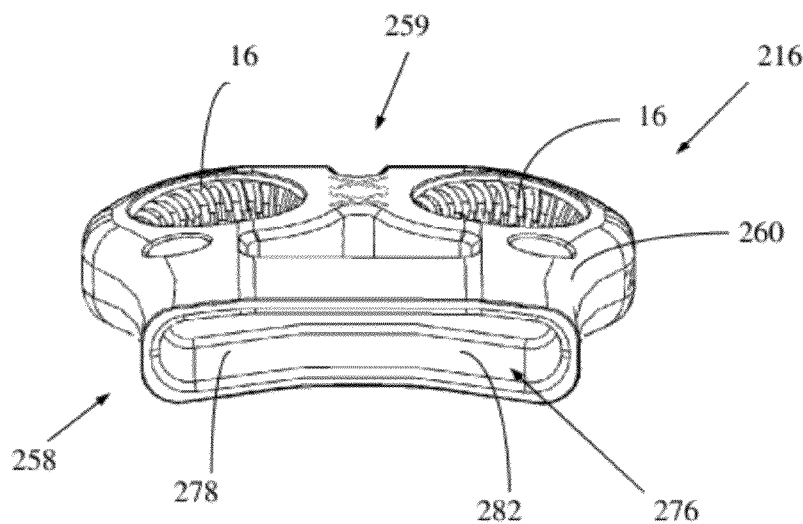
FIGS. 32-33 are perspective views of the end plate member of FIG. 29.
Figure 33:
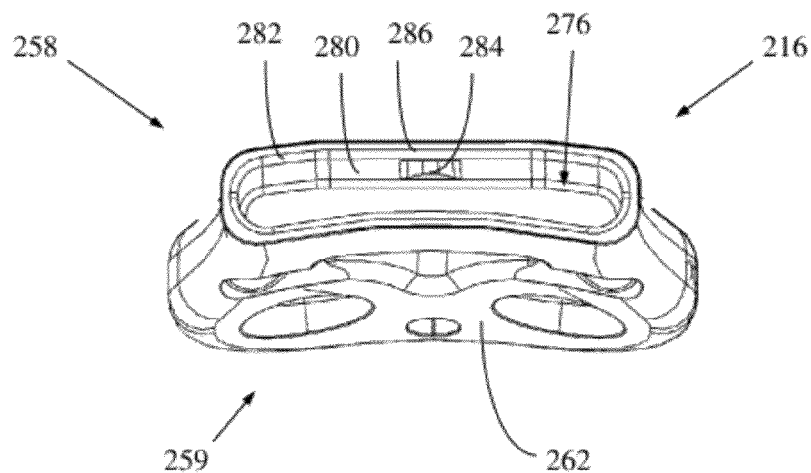
Figure 34:
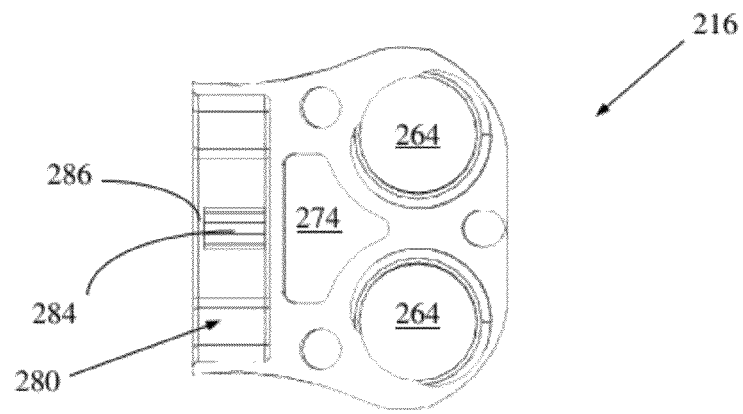
FIG. 34 is a partial cross-sectional view of the end plate member of FIG. 29.
Figure 35:
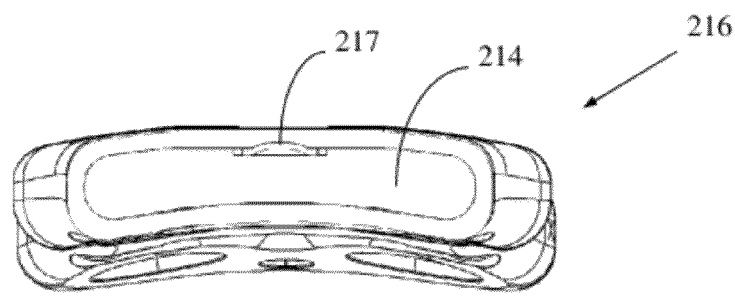
FIG. 35 is a cross-sectional view of the assembled surgical fixation plate of FIG. 18.
Figure 36:
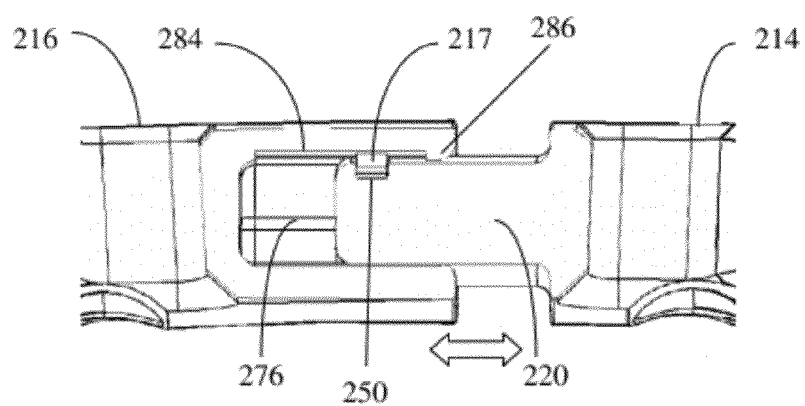
FIG. 36 is a partial cross-sectional view of the assembled surgical fixation plate of FIG. 18.
Figure 37:
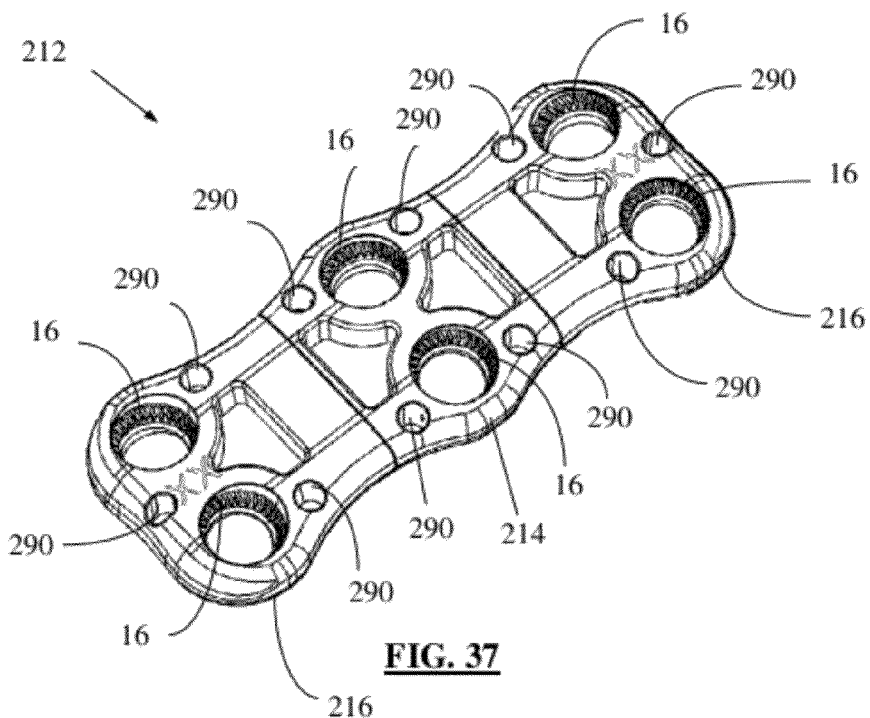
FIG. 37 is a perspective view of the assembled surgical fixation plate of FIG. 18.
Figure 38:
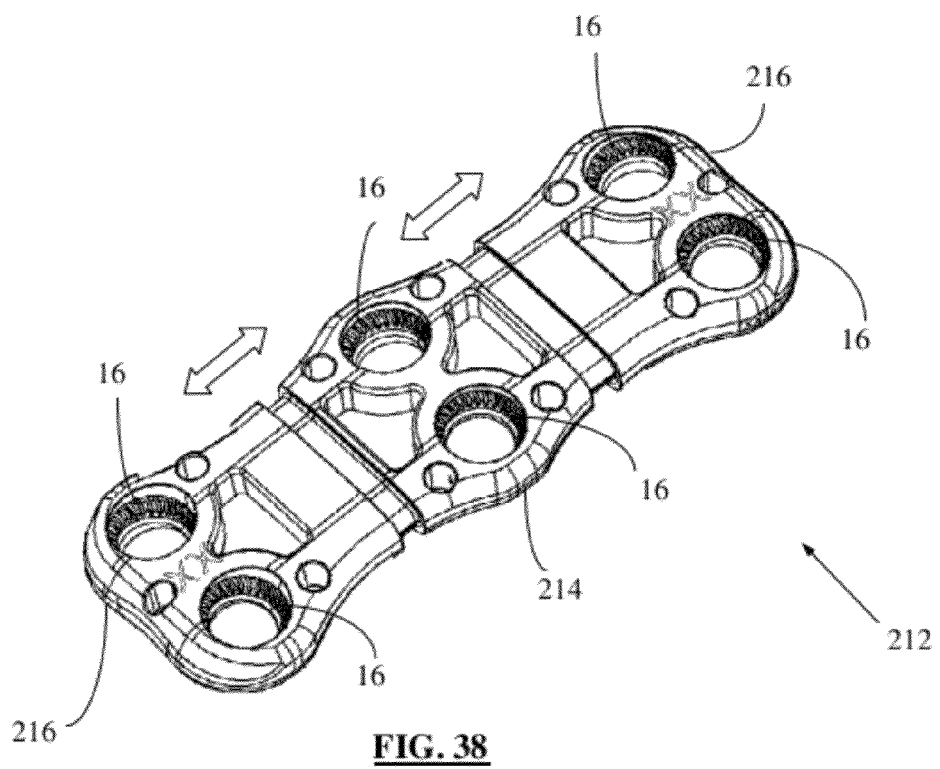
FIG. 38 is a perspective view of the assembled surgical fixation plate of FIG. 18, illustrating translation of the end plate members relative to the interior plate member.
Figure 39:
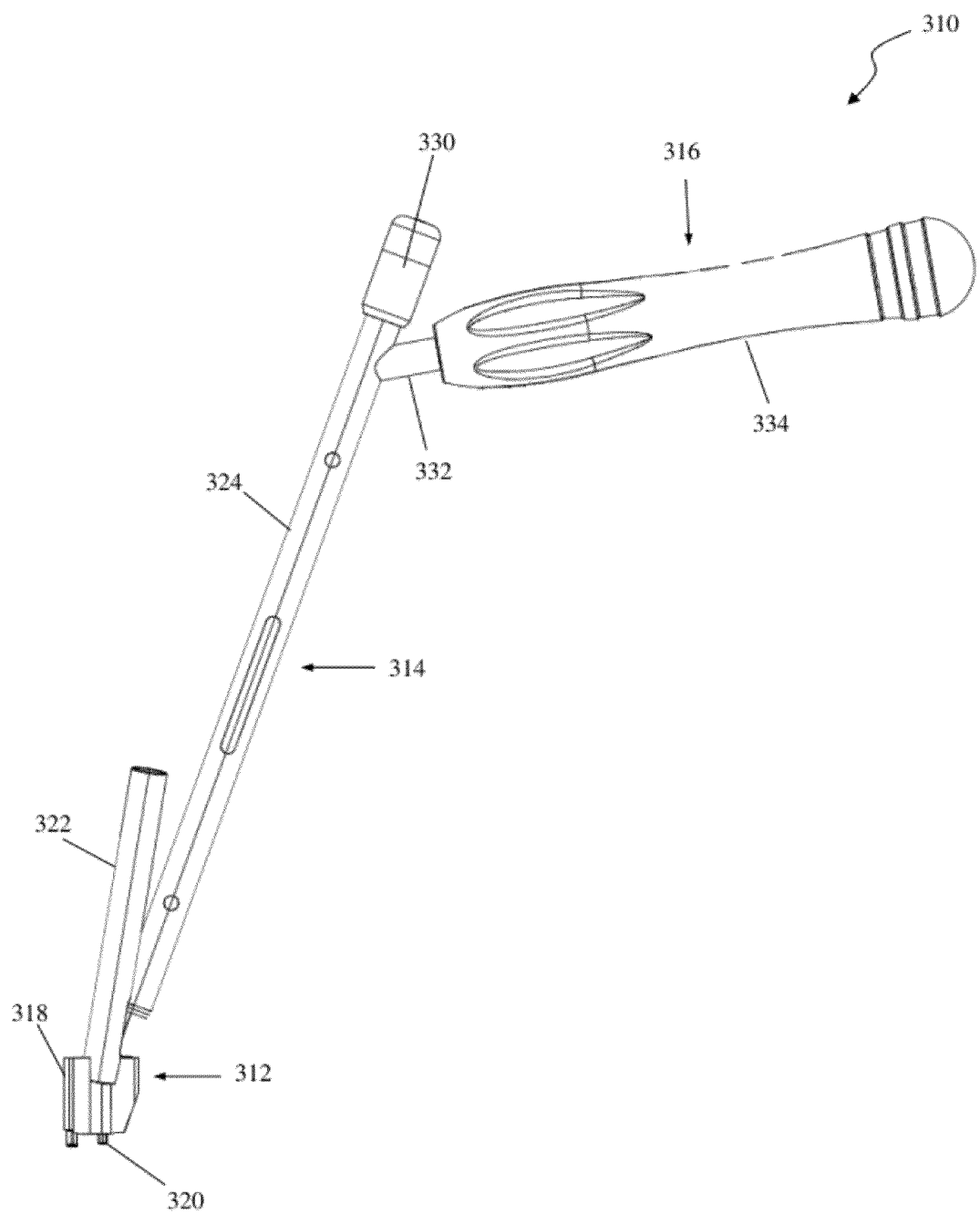
FIG. 39 is a plan view of an example of a DTS guide configured for use with a surgical fixation system of FIG. 18 according to one embodiment of the present invention.
Figure 40:
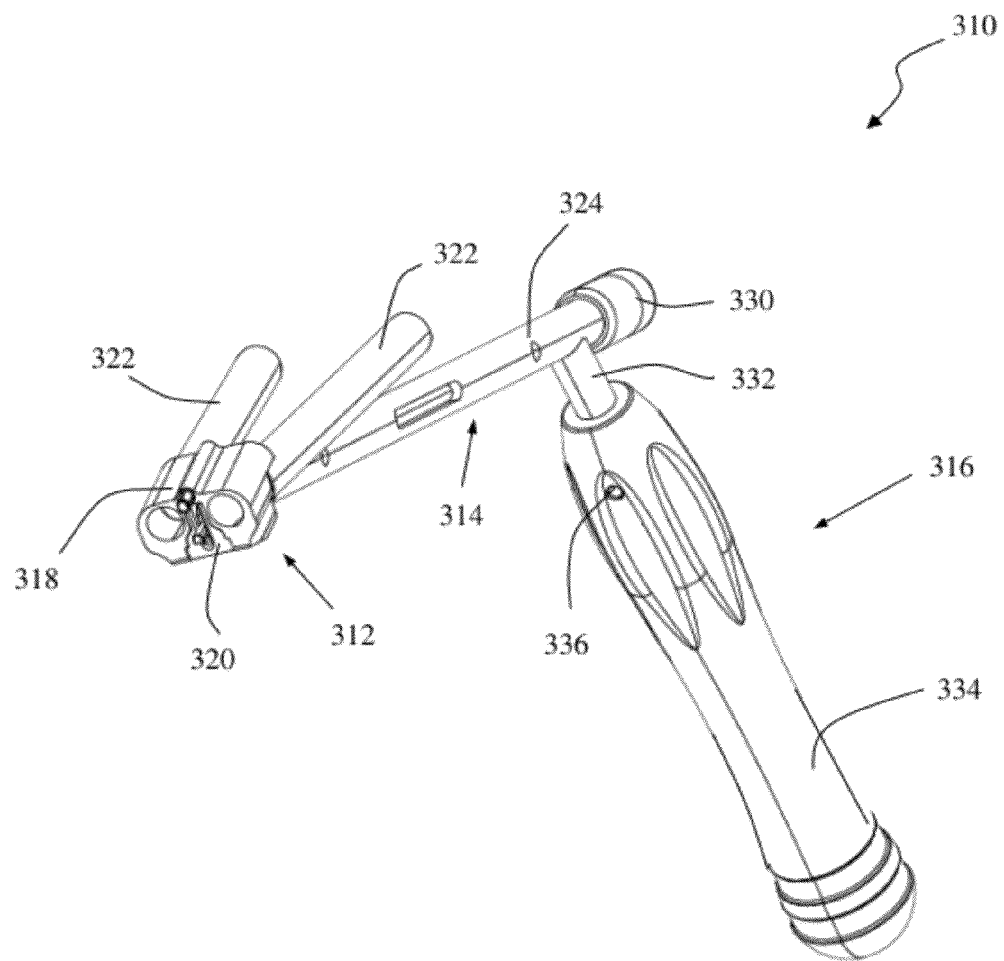
FIG. 40 is a perspective view of the DTS guide of FIG. 39.
Figure 41:
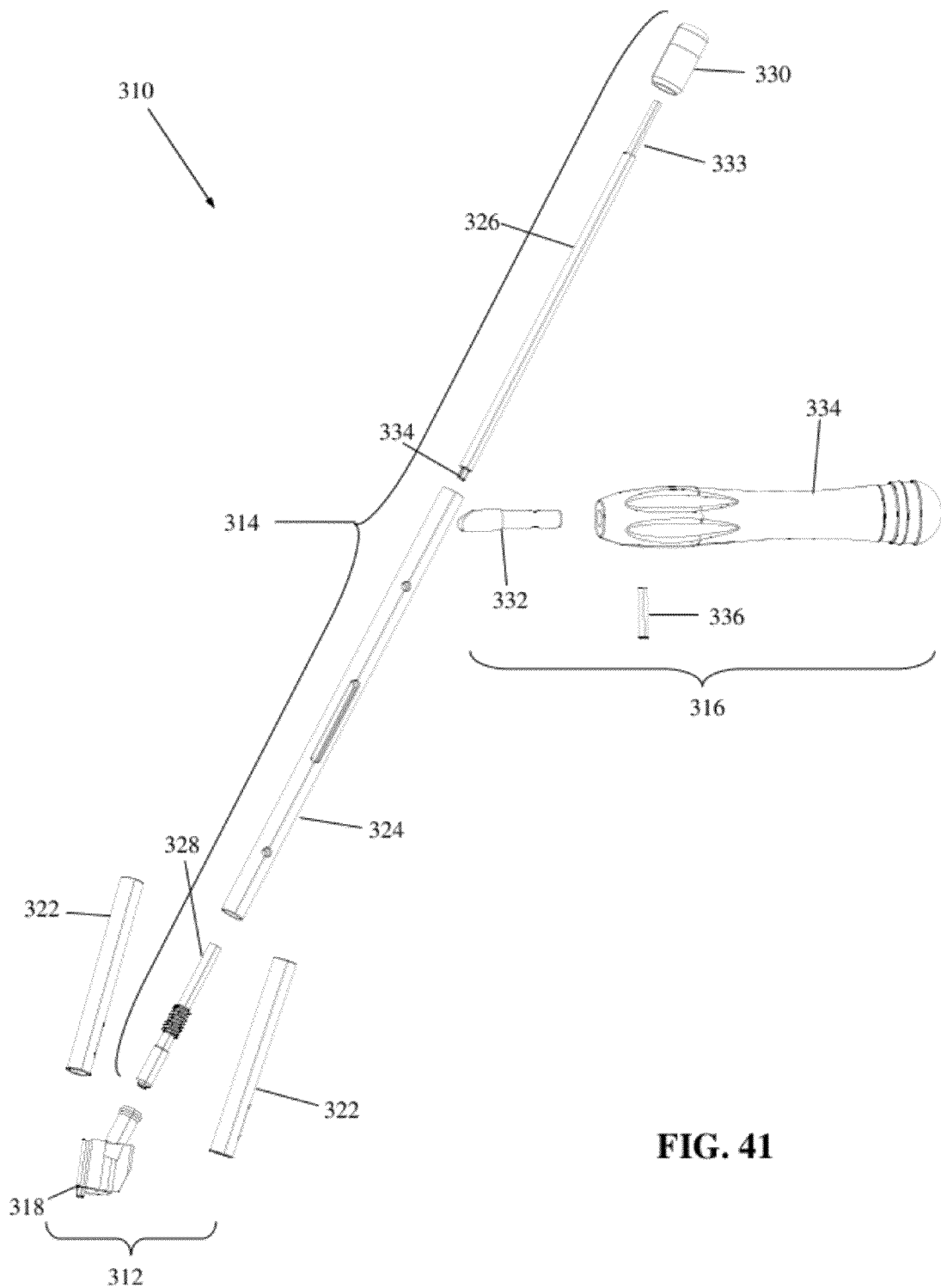
FIG. 41 is an exploded plan view of the DTS guide of FIG. 39.
Figure 42:
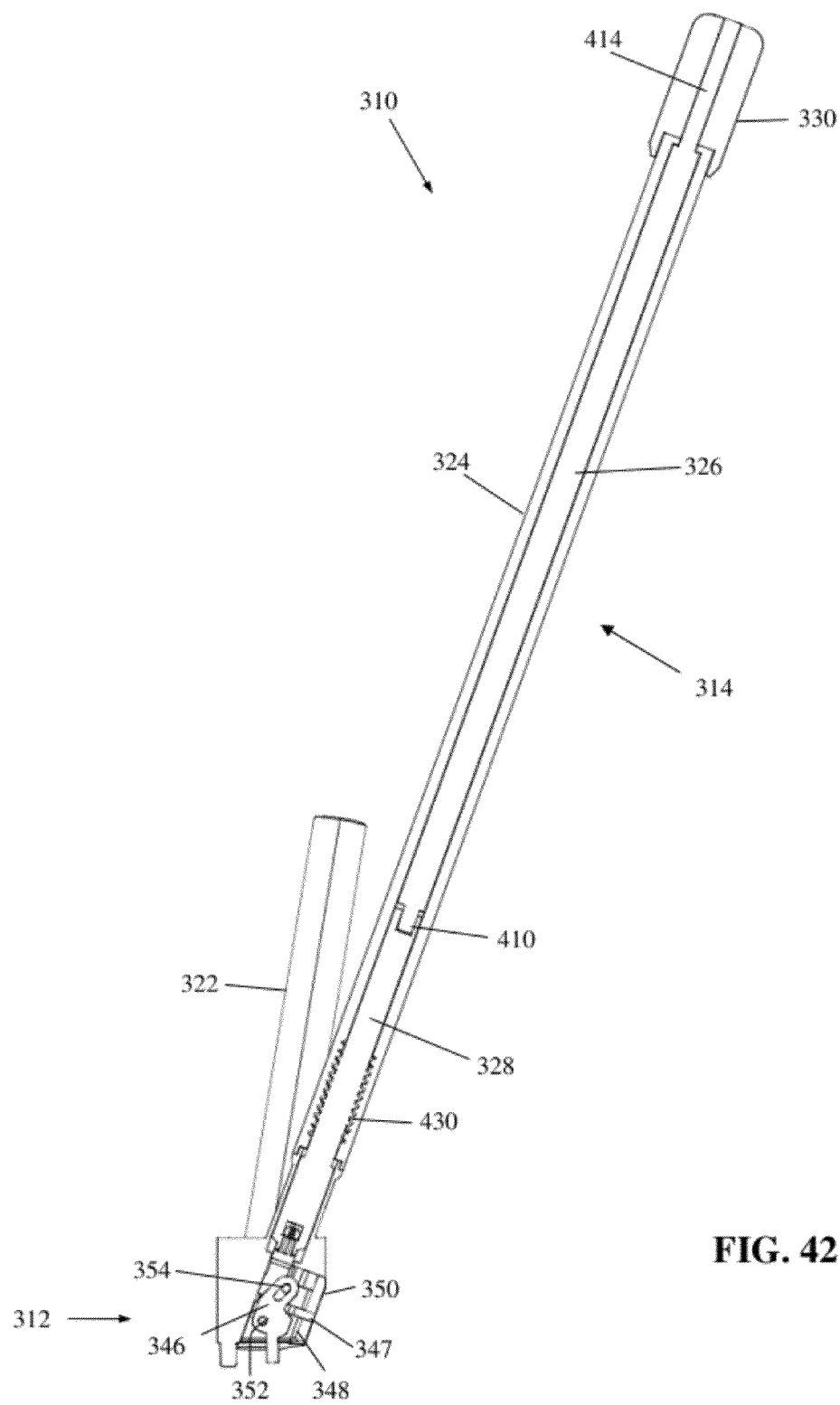
FIG. 42 is a cross-sectional view of the head of a DTS guide of FIG. 39 without the contoured handle.

FIGS. 32-34 illustrate the proximal end 258 of the end plate 216. Proximal end 258 includes a hollow receiving area 276 positioned between the first surface 260 and second surface 262. The hollow receiving area 276 includes a lower interior surface 278, and upper interior surface 280, and an opening 282. The hollow receiving area 276 is sized and dimensioned to slidingly receive the entirety of extension 220 of interior plate 214. The lower interior surface 278 is dimensioned to interact with the second surface 248 of the extension 220, and the upper interior surface 280 is dimensioned to interact with the first surface 246 of extension 220. Upper surface 280 further includes an elongated recess 284 positioned in the approximate middle thereof. Recess 284 is dimensioned to receive the raised generally planar central portion 252 and generally convex portions 254 of the spring member 217 when the interior plate 214 and end plate 216 are coupled together. Specifically, the recess 284 functions as a "track" for the spring member 217 to migrate within while the end plate 216 is translating relative to the interior plate 214. Furthermore, the end plate 216 includes a wall portion 286 positioned between the elongated recess 284 and the opening 282 that functions to block passage of the spring member 217 and therefore prevent the end plate 216 from uncoupling with the interior plate 214 once assembled.

FIGS. 35-38 illustrate the coupling of the interior plate 214 and end plate(s) 216, along with the translational properties of the surgical fixation plate assembly 210. To assemble the construct, a spring member 217 is placed within the recess 250 on the extension 220 of the interior plate 214. A downward force is applied to the spring member 217 to urge the spring member 217 fully into the recess 250. At this point the extension 220 is inserted into a receiving area 276 of an end plate 216 via opening 282. After the recess 250 including the spring member 217 is advanced beyond the wall portion 286 of the end plate 216, the spring member 217 returns to its "normal" positioning with the raised planar portion 252 extending into recess 284 of the hollow receiving are 276. Due to the inability of the spring member 217 to pass beyond the wall portion 286, the interior plate 214 and end plate 216 are now effectively coupled together. The extension 220 is free to bi-directionally translate within the hollow receiving area 276 in the distal and proximal directions. The other end plate 216 is added in the same manner to form the surgical fixation plate assembly 212 shown in FIGS. 37 and 38.

The amount of translation that takes place is determined by the length of the extensions 220 and corresponding size of the hollow receiving areas 276. By way of example only, this length may be within the range of 0.5 mm to 5.0 mm, and preferably within the range of 1 mm to 2 mm. The plate assembly 212 may be provided having any number of different peripheral profiles, including but not limited to the generally rectangular peripheral profile set forth by way of example in the figures (and best viewed in FIG. 37).

In addition to the viewing apertures 234, 274, the plate assembly 212 may be configured to include at least one insertion aperture 290 provided at either end of the plate assembly 212 for receiving at least a portion of an insertion instrument. By way of example only, the plate assembly 212 shown in the attached figures includes a plurality of insertion apertures 290, distributed about the periphery of the plate assembly 212. The insertion apertures 290 may be configured to engage at least a portion of an insertion device (not shown), and thus may include any suitable feature necessary to allow such engagement, including but not limited to threading, ridges, and recesses.

In all the embodiments described herein, the anti-backout element functions to resist backout tendencies in bone screws. The anti-backout element does not, however, lock a bone screw to a plate. This is because the bone screw is removable from the bone screw aperture through application of a sufficient amount of force to pull the lip member (or washer) through the anti-backout member. Due to the nature of the canted coil ring and dimensions of the lip member (or washer) described above, the force required to remove an inserted bone screw is greater than the force required to insert the bone screw. Nevertheless, the bone screw may be inserted and/or removed in a single-step process—no separate manipulation of the anti-backout element is required.

FIGS. 39-42 illustrate an example of a drill, tap, and screw (DTS) guide 310 according to one embodiment of the present invention. The DTS guide 310 described herein is sized and dimensioned to assist in implanting a plate and screws (for example the surgical fixation system 210 described above) within a body. The DTS guide 310 includes an engagement assembly 312, an elongated body portion 314, and a handle member 316. The engagement assembly 312 is located at a distal end of the elongated body portion 314, and the handle member 316 extends from a proximal end of the elongated body portion 314. As will be explained in further detail below, the engagement assembly 312 is operable to releasably grab and hold a portion of a bone fixation plate, for example a portion of the surgical fixation system 210. The elongated body portion is sized and dimensioned to extend through an operative corridor to a surgical target site within a body. The handle member 316 remains outside the body to enable operation of the DTS guide by a user.

The engagement assembly 312 further includes a housing 318, actuator 320, and a pair of guide tubes 322 extending in a proximal direction from the housing 318. The elongated body portion 314 further includes an outer tube 324, an inner shaft 326, a connector 328, and a thumbwheel 330. The handle member 316 further includes a handle shaft 332, a contoured handle 334, and a pin 336.

Figure 43:
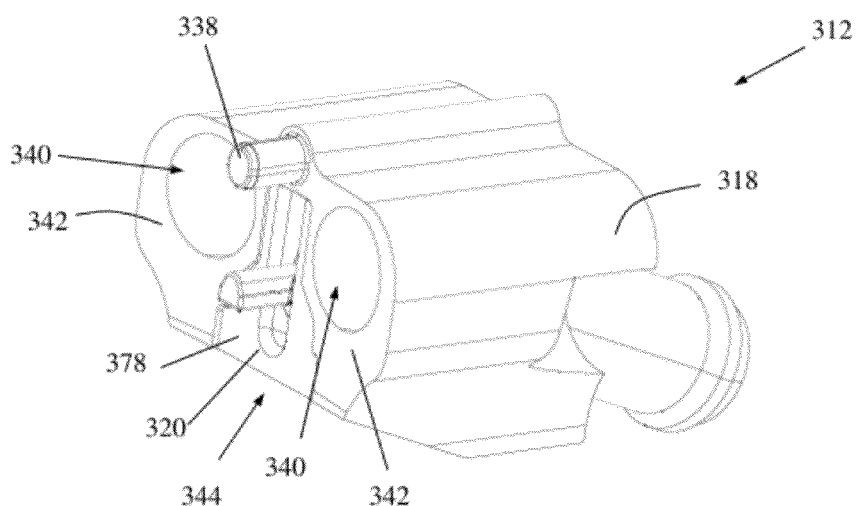
FIG. 43 is a perspective view of an engagement assembly forming part of the DTS guide of FIG. 39.
Figure 44:
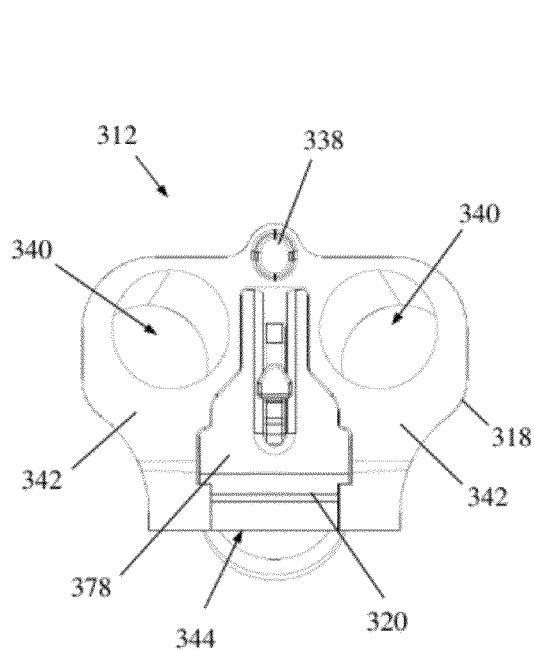
FIG. 44 is a plan view of the distal end of the engagement assembly of FIG. 42.
Figure 45:
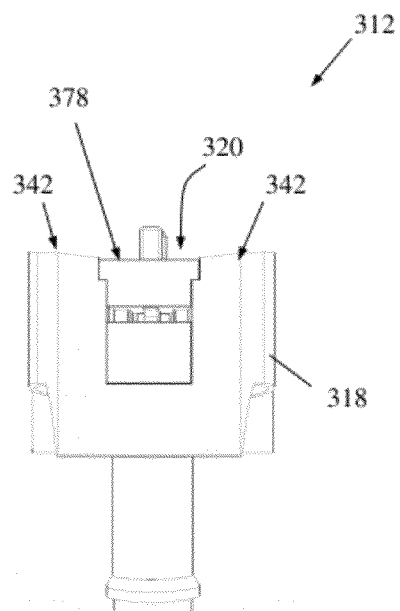
FIG. 45 is a plan view of the engagement assembly of FIG. 42.
Figure 46:
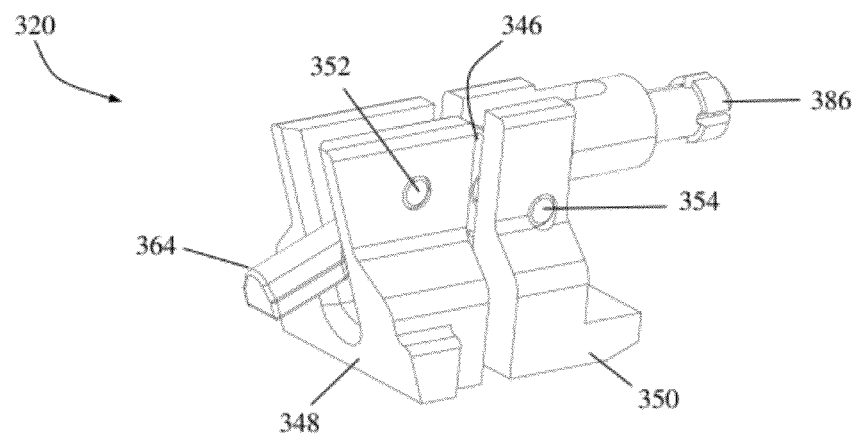
FIG. 46 is a perspective view of an actuator forming part of the engagement assembly of FIG. 43.
Figure 47:
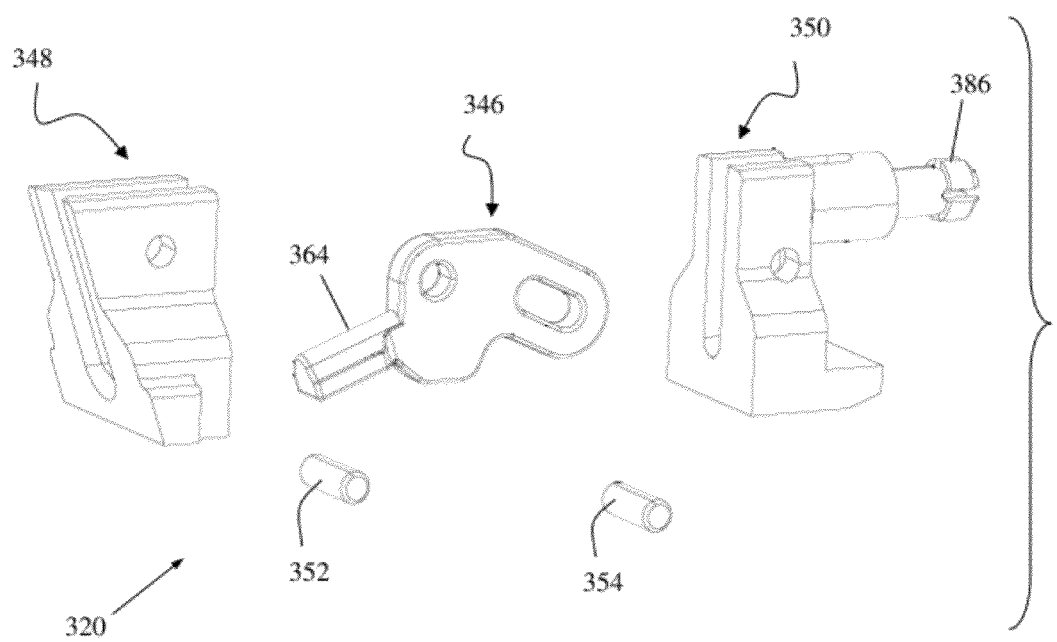
FIG. 47 is an exploded perspective view of the actuator of FIG. 46.
Figure 48:
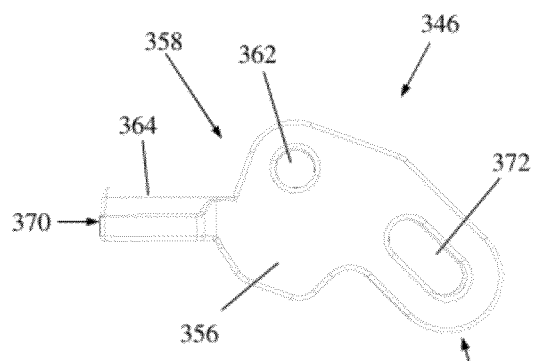
FIGS. 48-49 are side plan and end plan views, respectively, of a pivot member forming part of the actuator of FIG. 46.
Figure 49:
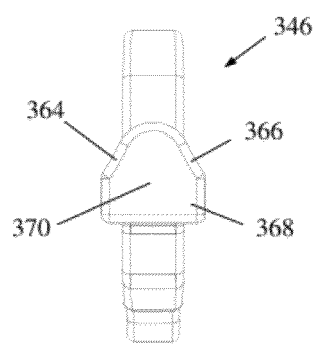

The engagement assembly 312 will now be described in further detail with specific reference to FIGS. 43-53. Referring first to FIGS. 43-45, the housing 318 includes a boss 338 positioned along the midline of the housing 318 and a pair of apertures 340 positioned on either side of the midline of the housing 318. In the example shown in FIG. 43, the boss 338 is positioned on one side of the housing 318 and extends distally outward from the housing 318. By way of example only, the boss 338 may be provided with one or more anti-migration features (e.g. surface roughening, spikes, etc.) that enable the boss 338 to grip to a bony segment to give the surgeon more control when using the DTS guide 310. The boss 338 is generally configured to conform to an aperture in a bone plate 430 (FIGS. 62-65). As shown by way of example only, the boss 338 has a generally cylindrical shape (having a generally circular cross-section), however any shape is possible so long as the boss 338 is capable of engaging the relevant bone plate.

The housing 318 further includes a distal engagement surface 342 and a central recess 344. The distal engagement surface 342 is a generally curved surface and is configured to interface with the upper surface of the bone plate to which the DTS guide 310 engages. The central recess 344 is sized and configured to securely receive the actuator 320 therein. The apertures 340 are configured align with the bone screw apertures of the bone plate 430 and to further mate with the guide tubes 322 such that the surgeon has a clear linear path through which to insert a drill, tap or bone screw. In order to ensure that the bone screws are inserted in a convergent orientation within the bone, the apertures 340 are configured such that longitudinal axes extending through each of the apertures 340 are not parallel, but rather are convergent in a distal direction (and therefore divergent in a proximal direction). The guide tubes 322 may be provided in any length sufficient to enable a proper alignment of the instruments used therewith.

Referring to FIGS. 46-52, the actuator 320 will now be described in further detail. The actuator 320 further includes pivot member 346, a first housing portion 348, and a second housing portion 350. As will be explained in greater detail below, the pivot member 346 is positioned within and between the first and second housing portions 348, 350 and connected thereto by first and second pins 352, 354. The first pin 352 operates to connect the pivot member 346 to the first housing portion 348. The second pin 354 operates to connect the pivot member 346 to the second housing portion 350. As shown by way of example, the first and second pins 352, 354 are generally cylindrical in shape, however other shapes are possible without departing from the scope of the present invention. Further functions of the pins 352, 354 are described in detail below.

The pivot member 346 includes a body 356 including a distal end 358 and a proximal end 360. The distal end 358 includes a first aperture 362 dimensioned to receive the first pin 352 therethrough, and a flange 364 extending distally away from the body 356. By way of example only, the first aperture 362 is generally circular in shape such that the first pin 352 fits snugly with in the first aperture 362 and further such that the pivot member 346 is able to pivot about the first pin 352. By way of example only, the flange 364 may be provided with a first edge portion 366 and a second edge portion 368, which cooperate to form the perimeter of the flange 364. In the example provided herein, the first edge portion 366 has a curved shape to cooperate with the second aperture 436 of the bone plate 430 (FIG. 62), however other shapes are possible. The second edge portion 368 may have any shape without departing from the scope of the present invention, including the squared shape shown by way of example in FIG. 49. As will be described below, the first edge portion 366 engages the bone plate 430 when the DTS guide 310 is in use. The flange 364 further includes a planar surface 370 and the distal end of the flange 364.

The proximal end 360 of the pivot member 346 includes a second aperture 372 dimensioned to receive the second pin 354 therethrough. Unlike the first aperture 362, the second aperture 362 is in the form of an elongated oval such that the pivot member 346 is able to move relative to the second pin 354 with the DTS guide 310 is in use.

Figure 50:
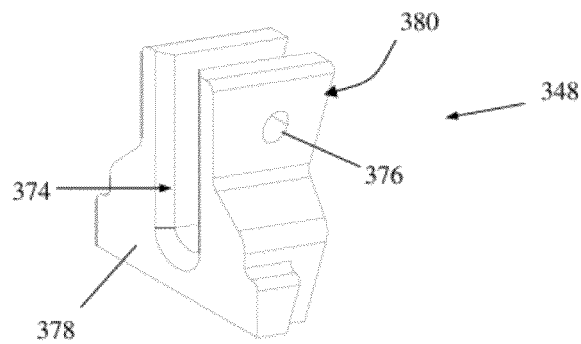
FIG. 50 is a perspective view of a first housing portion forming part of the actuator of FIG. 46.

Referring to FIG. 50, the first housing portion 348 includes a U-shaped groove 374 and a circular aperture 376 on each side of groove 374. The groove 374 is dimensioned to receive the distal end 358 of the pivot member 346 and allow for movement of the pivot member 346 within the groove 374. A substantial portion of the flange 364 extends distally from the groove 374. The circular apertures 376 are axially aligned with one another and are positioned to be axially aligned with the first aperture 362 of the pivot member 346. When assembled, the first pin 352 extends axially through the circular apertures 376 of the first housing portion 348 and the first aperture 362 of the pivot member 346, effectively connecting the pivot member 346 and the first housing portion 348. The first housing portion 348 includes a distal engagement surface 378 and a proximal engagement surface 380. The distal engagement surface 378 creates a smooth continuation of the distal engagement surface 342 of the housing 318 (best illustrated in FIGS. 43-45). Thus, the distal engagement surface 378 is a generally curved surface and is configured to interface with the upper surface of the bone plate to which the DTS guide 310 engages. The proximal engagement surface 380 faces the second housing portion 350 and is configured to interface with the distal engagement surface 385 of the second housing portion 350 when the DTS guide 310 is in a second, actuated position (as described in further detail below).

Figure 51:
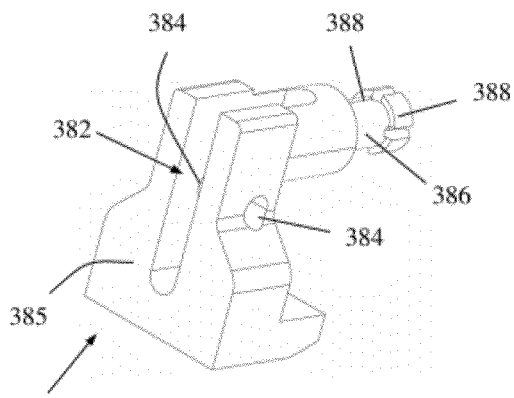
FIGS. 51-52 are perspective and plan views, respectively, of a second housing portion forming part of the actuator of FIG. 46.
Figure 52:
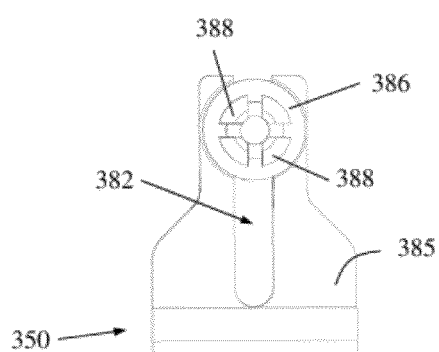
Figure 53:
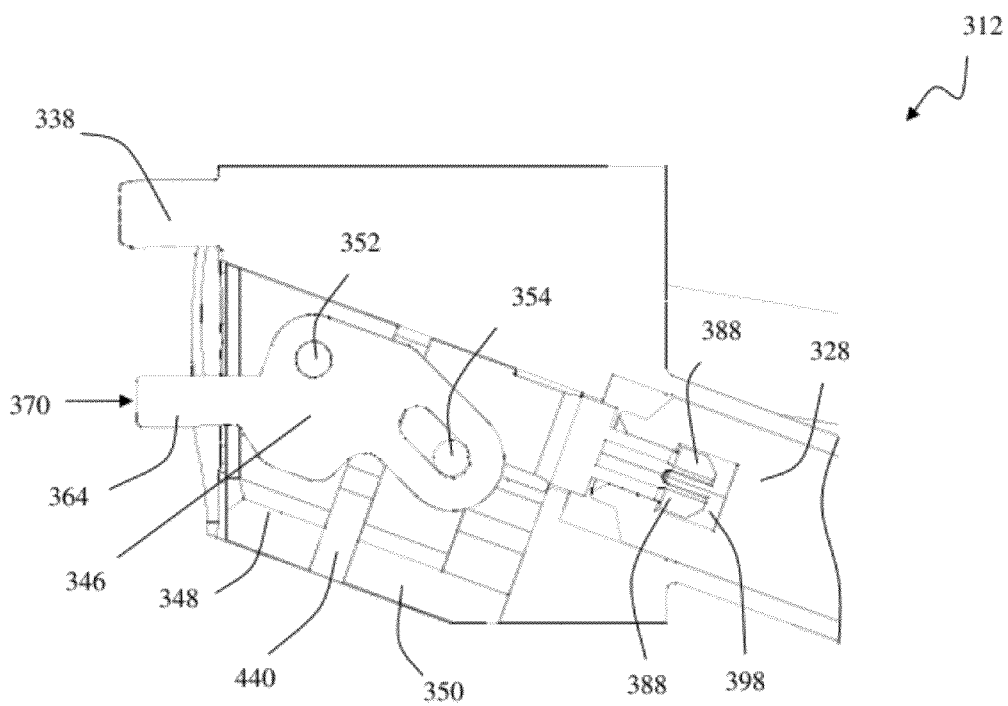
FIG. 53 is an enlarged cross-sectional view of the engagement assembly of FIG. 42.

Referring to FIGS. 51-52, the second housing portion 350 includes a U-shaped groove 382, a pair of apertures 384 located on either side of the groove 382, and a connecting flange 386 extending in a proximal direction from the second housing portion 350. The groove 382 is dimensioned to receive the proximal end 360 of the pivot member 346 and allow for movement of the pivot member 346 within the groove 382. The circular apertures 384 are axially aligned with one another and are positioned to be axially aligned with the second aperture 372 of the pivot member 346, effectively connecting the pivot member 346 and the second housing portion 350. The second housing portion 350 further includes a distal engagement surface 385 that faces the first housing portion 348 and is configured to interface with the proximal engagement surface 380 of the first housing portion 348 when the DTS guide 310 is in a second, actuated position (as described in further detail below). The connecting flange 386 is dimensioned to provide a connection between the engagement assembly 312 and elongated body portion 314. By way of example only, the connecting flange 386 includes deflectable snap members 388 that connect to a circular opening 396, located at the proximal end of connector 328, and sit within the undercut 398 of the connector 328, as described in greater detail below.

Figure 54:
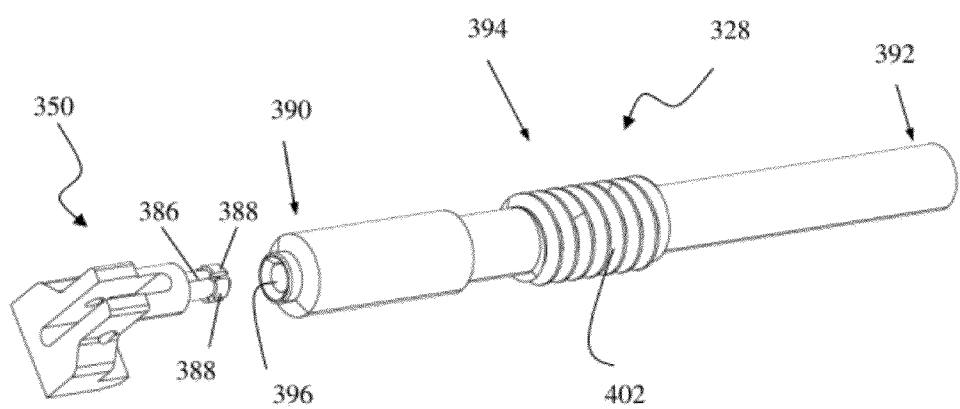
FIG. 54 is a perspective view of the second housing portion of FIG. 51 prior to coupling with a connector forming part of the DTS guide of FIG. 39.
Figure 55:
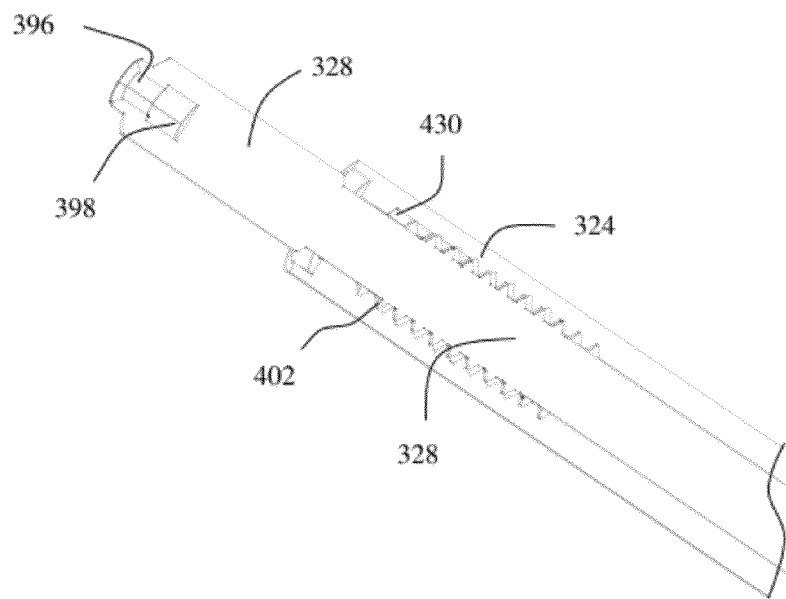
FIG. 55 is an enlarged cross-sectional view of the distal region of an elongated body portion forming part of the DTS guide of FIG. 39.
Figure 56:
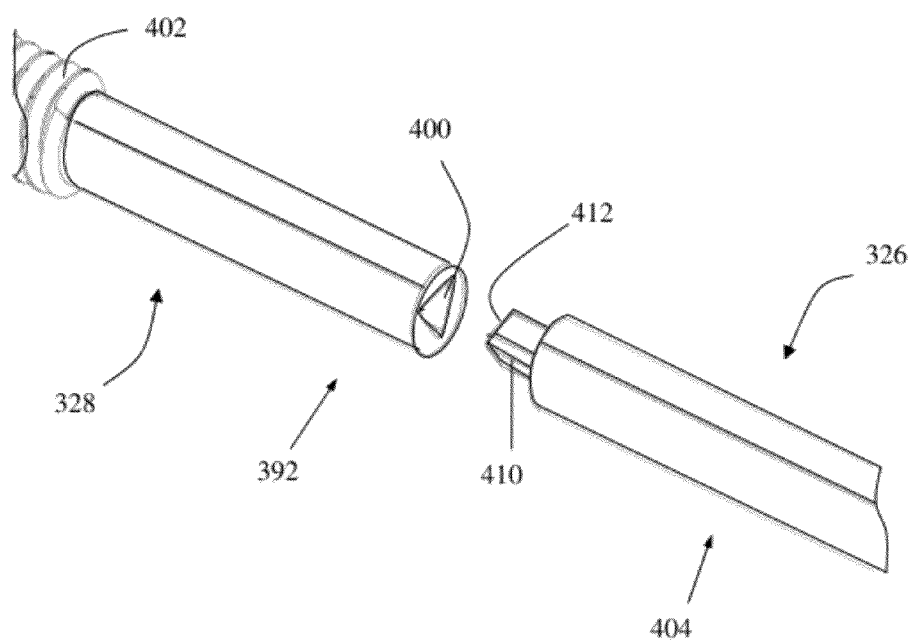
FIG. 56 is a perspective view distal end of the connector of FIG. 54 prior to coupling to the inner shaft forming part of the DTS guide of FIG. 39.

The elongated body portion 314 will now be described in further detail with specific reference to FIGS. 54-59. Referring first to FIGS. 54-56, the connector 328 is an elongated, generally cylindrical member having a longitudinal axis extending therethrough, and further having a distal end 390, a proximal end 392, and an elongated shaft 394 extending therebetween. The distal end 390 includes a circular opening 396 and an undercut 398 formed within the distal end 390 and extending proximally into the connector 328 along the longitudinal axis, as shown in FIG. 55. The circular opening 396 has a smaller diameter than the undercut 398, and is dimensioned to receive the deflectable snap members 388 of the connecting flange 386 of the second housing portion 350 therethrough, as previously mentioned. To accomplish this, the deflectable snap members 388 are compressed as they pass through the circular opening 396, and then expanded when they pass into the undercut 398. When expanded in this fashion, the engagement assembly 312 is connected to the elongated body portion 314. To disassemble, a sufficient force is applied in a distal direction to cause the deflectable snap members 388 to compress again and pass through the circular opening 396.

The proximal end 392 includes an aperture 400 formed therein and extending distally into the connector 328 along the longitudinal axis. The aperture 400 has a polygonal cross-sectional shape and is dimensioned to receive the distal boss 410 of the inner shaft 326, as will be described further below. By way of example only, the aperture 400 is provided with a triangular cross-section, however other shapes are possible without departing from the scope of the present invention. The elongated shaft 394 has a threaded portion 402 located generally in the middle of the elongated shaft 394. The threaded portion 402 threadedly engages the threaded portion 430 of the outer tube 324.

Figure 57:
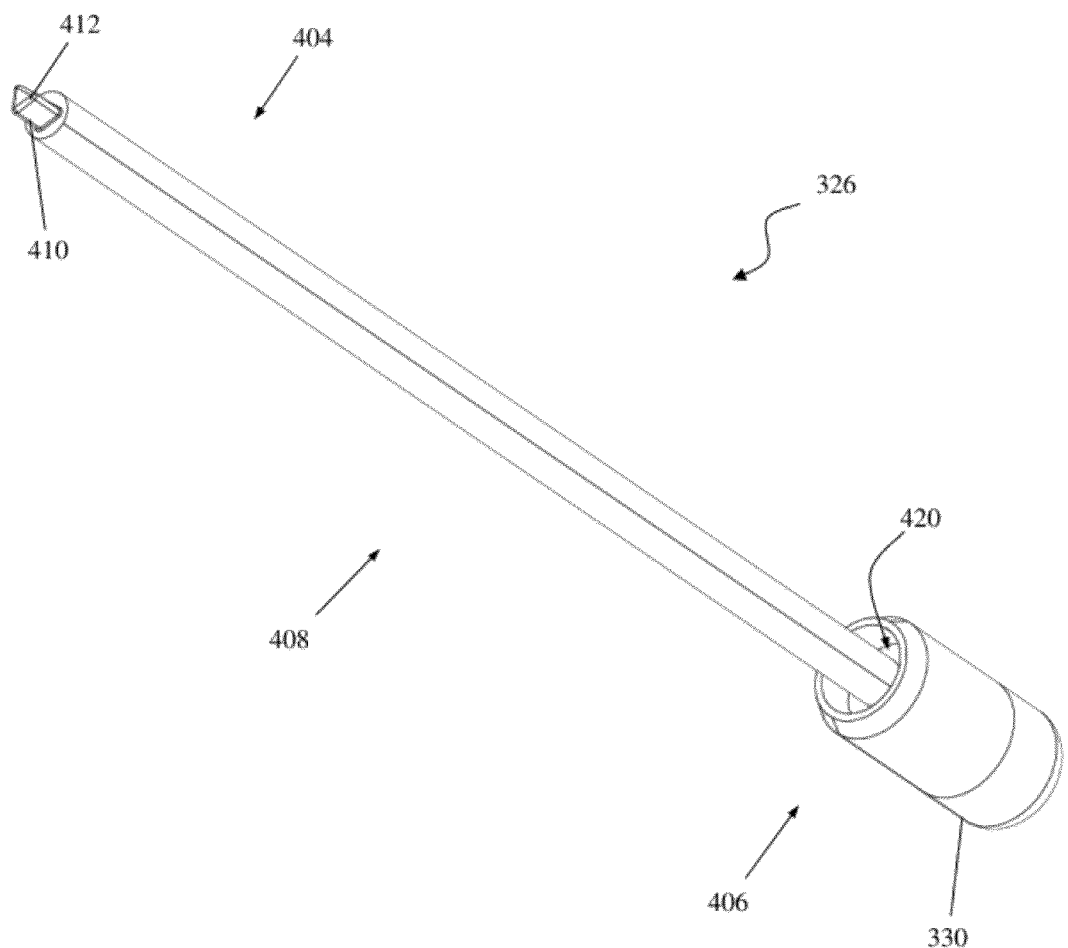
FIG. 57 is a perspective view of the inner shaft and thumbwheel forming part of the DTS guide of FIG. 39.
Figure 58:
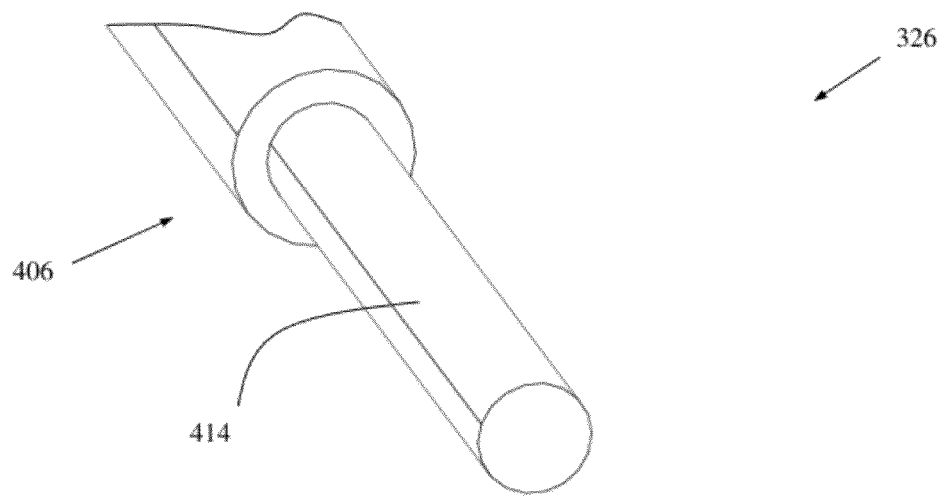
FIG. 58 is an enlarged view of the distal end of the inner shaft of FIG. 57.
Figure 59:
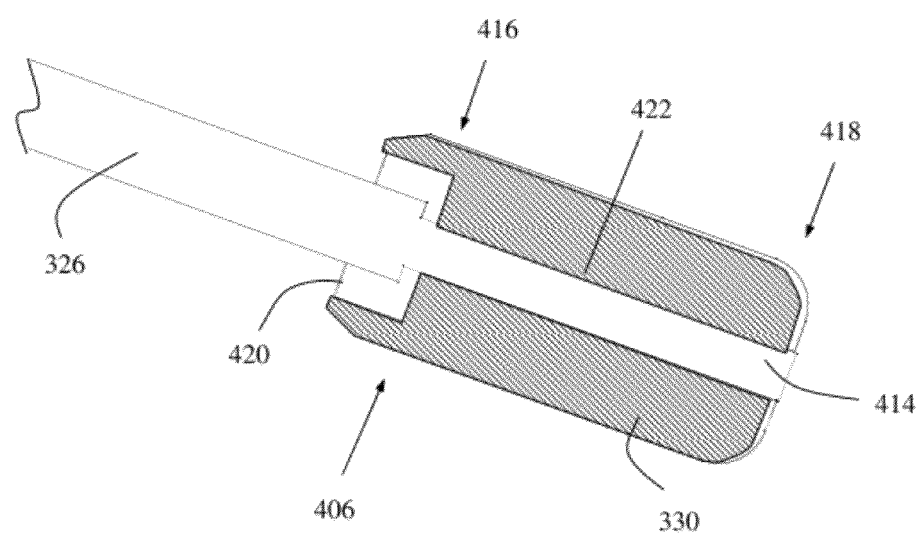
FIG. 59 is a cross-sectional view of the engagement between the inner shaft and thumbwheel of FIG. 57.

Now referring to FIGS. 57-59, the inner shaft 326 is an elongated generally cylindrical member having a longitudinal axis extending therethrough and further having a distal end 404, a proximal end 406, and a body portion 408 extending therebetween. The distal end 404 has a distal boss 410 extending distally therefrom along the longitudinal axis of the inner shaft 326. The distal boss 410 has a polygonal cross-section that corresponds to the cross-section of the aperture 400 of the connector 328. By way of example only, the distal boss 410 has a triangular cross-section, however other shapes are possible. As will be described in further detail below, as the inner shaft 326 is rotated, the distal boss 410 creates a torque on the aperture 400, thereby causing the connector 328 to rotate in the same direction as the inner shaft 326. During this rotation, the connector 328 migrates axially relative to distal boss 410 such that the terminal end of the distal boss 410 slides axially into and out of the aperture 400. The proximal end 406 includes a cylindrical shaped projection 414 extending axially therefrom in a proximal direction along the longitudinal axis of the inner shaft 326.

The thumbwheel 330 is a generally cylindrical shaped member that is configured to allow a user to operate the DTS guide 310 as desired. The thumbwheel 330 has a distal end 416 and a proximal end 418. The thumbwheel further has a recess 420 and a central lumen 422 extending axially through the thumbwheel 330 from the recess 420 to the proximal end 418. The recess 420 is dimensioned to receive the outer tube 324 therein. Although not shown, the thumbwheel 330 may be further provided with surface roughening or other suitable frictional element to allow a user to operate the thumbwheel 330.

Figure 60:
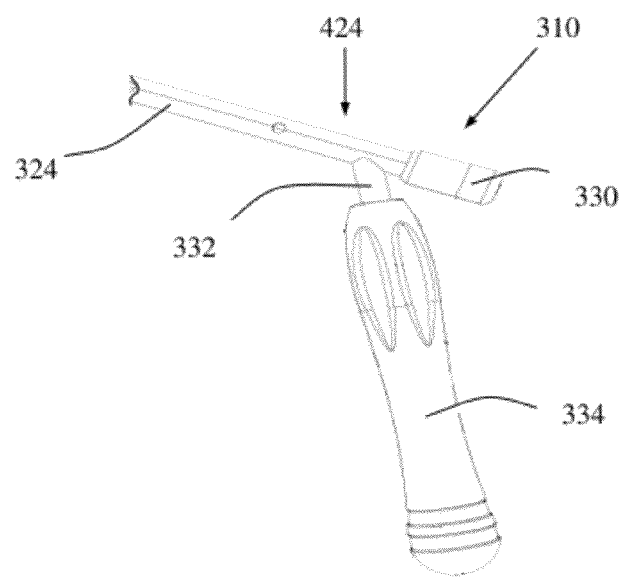
FIG. 60 is an plan view of the distal region of the outer body shaft, thumbwheel, and contoured handle of the DTS guide of FIG. 39.
Figure 61:
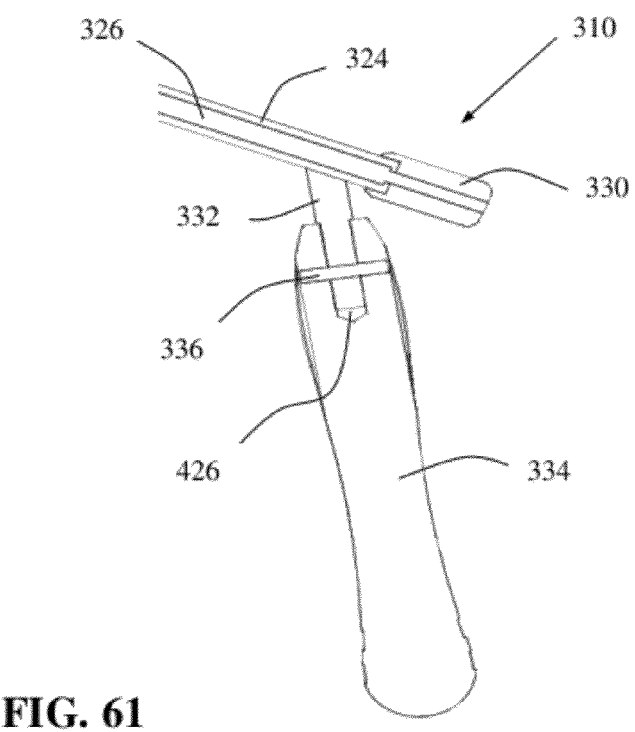
FIG. 61 is a cross-sectional view of the distal region of the outer body shaft, thumbwheel, and contoured handle of FIG. 60.
Figure 62:
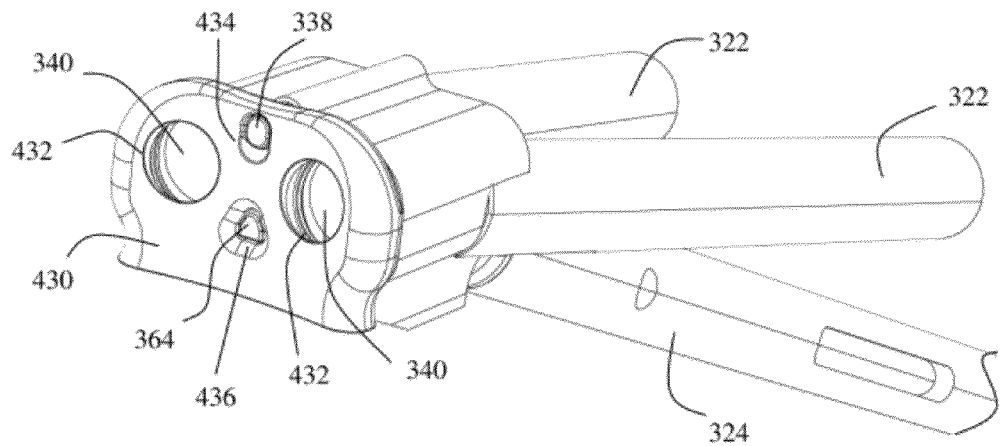
FIG. 62 is a perspective view of the engagement assembly of the DTS guide engaged in an unlocked position with a first portion of a bone plate.

Referring to FIGS. 60-61, the handle member 316 will now be described in further detail. The handle member 316 includes a handle shaft 332 and a contoured handle 334. The handle shaft 332 is located at a distal end 424 of the outer tube 324 distally of the thumbwheel 330 and connects the contoured handle 334 to the outer tube 324. The handle shaft extends through a recess 426 in the contoured handle 334, and connects to the handle 334 with a pin 336. Contoured handle 334 may be sized and dimensioned to enable comfortable handling by the surgeon.

Referring again to FIG. 42, the outer tube 324 connects the engagement assembly 312 to the thumbwheel 330. The outer tube 324 includes a central lumen 426 extending axially and longitudinally therethrough. At a distal end 428 of the outer tube 324, the central lumen 426 includes a threaded portion 430 for threadedly engaging the threaded region 402 of the connector 328. The outer tube 324 also functions to enclose the various components of the elongated body portion 314.

Figure 63:
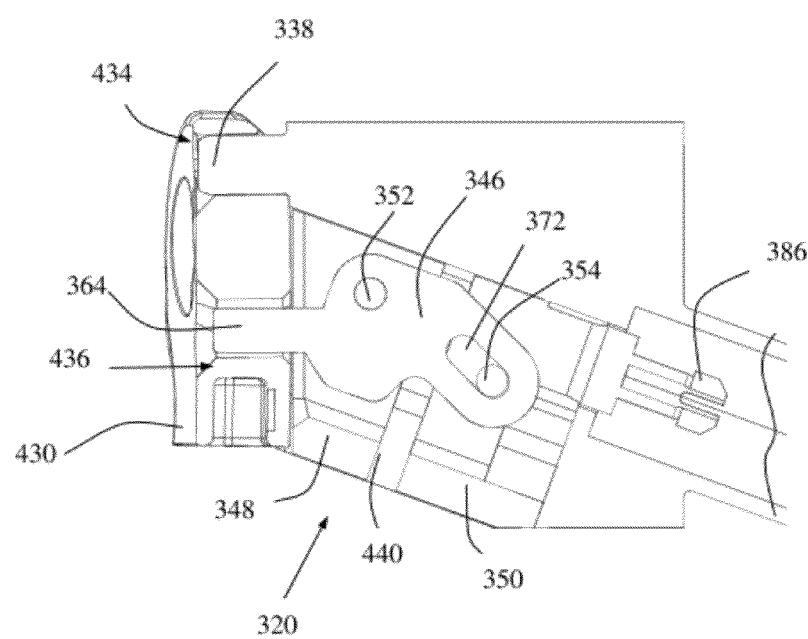
FIG. 63 is a cross-sectional view of the engagement assembly of the DTS guide engaged in an unlocked position with a first portion of a bone plate of FIG. 62.
Figure 64:
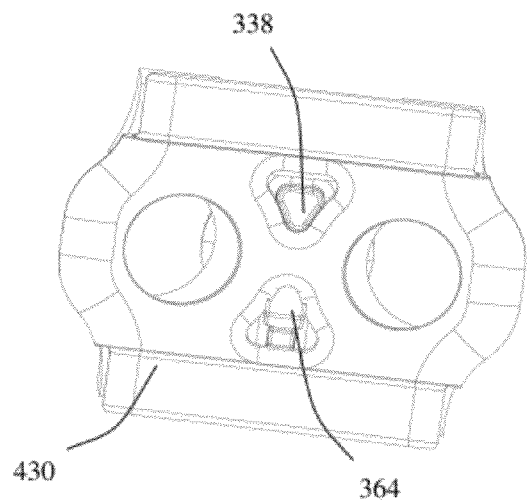
FIG. 64 is a the plan view of the engagement assembly of a DTS guide engaged in a locked position with a second portion of a bone plate.

FIGS. 62-65 illustrate the DTS guide 310 coupled to a portion of a bone plate 430. The bone plate 430 includes at least a pair of bone screw apertures 432 positioned near one end of the bone plate 430 on opposite sides of a longitudinal midline of the plate. The bone plate 430 further includes first and second engagement apertures 434, 436 positioned between the bone screw apertures 432 and aligned along the longitudinal midline of the plate. In order to use the DTS guide 310, a surgeon grips the contoured handle 330 with one hand and inserts the boss 338 of the housing 318 and flange 364 of the actuator 320 into first and second apertures 434, 436, respectively, of the bone plate 430. At this point, the DTS guide 310 is in a first position such that flange 364 and boss 338 are in a generally parallel orientation to one another, and the bone plate 430 is not secured to the DTS guide 310. As illustrated in FIG. 63, a space 440 exists between the first housing portion 348 and second housing portion 350 of the actuator 320. The second pin 354 is also positioned at a proximal end of the second aperture 372 of the pivot member 346.

Figure 65:
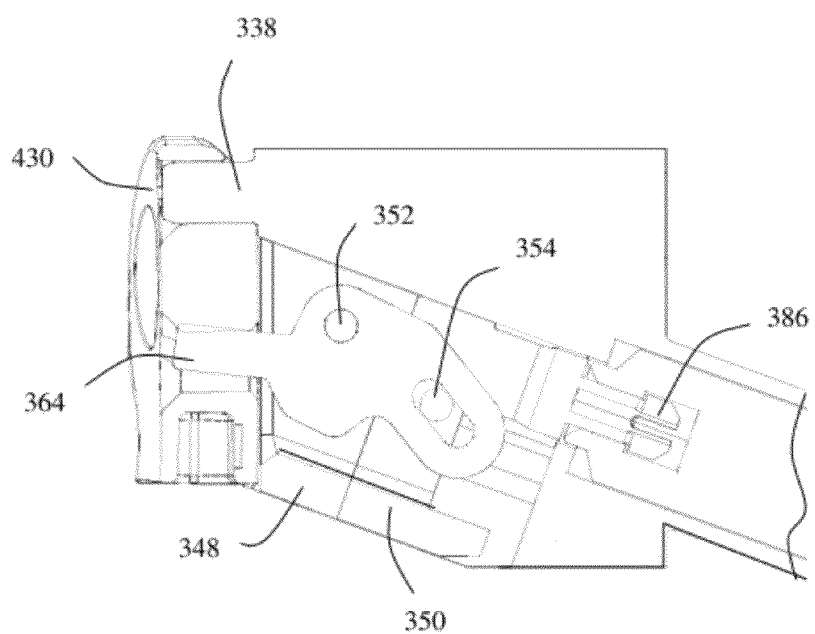
FIG. 65 is a cross-sectional view of an engagement assembly of a DTS guide engaged in a locked position with a first portion of a bone plate.

In order to operate the DTS guide 310, the surgeon rotates the thumbwheel 330 in a clockwise direction. As the thumbwheel 330 rotates (and referring again to FIG. 42), the inner shaft 326 will also rotate in the same (clockwise) direction. Due to the interaction between the distal boss 410 of the inner shaft 326 and the proximal aperture 400 of the connector 328, the connector 328 also rotates in a clockwise direction. As the connector 328 rotates, the interaction between the threaded portion 402 of the connector 328 and the threaded portion 430 of outer tube 324 (which is stationary) causes the connector 328 to migrate distally within the outer tube 324. Because the distal boss 410 of the inner shaft 326 is slideably engaged with the proximal aperture 400 of the connector 328, the distal boss 410 continues to apply the appropriate torque to turn the connector 328. Since the connector 328 is connected to the second housing portion 350 of the actuator 320 via the connecting flange 386, the distal migration of the connector 328 causes likewise distal migration of the second housing portion 350 until the gap 440 is closed. This distal migration of the second housing portion 350 causes a distal migration of the second pin 354 within the second aperture 372. Due to the angled orientation of the second aperture 372, distal migration of the second pin 354 therein causes the pivot member 346 to pivot around the first pin 352. This pivoting movement causes the flange 364 to migrate toward the boss 338 such that the flange 364 and boss 338 exert a compressive force on the bone plate 430. This is the second, actuated position of the DTS guide 310 (FIG. 65).

To release the plate 430 from the DTS guide 310, a surgeon rotates thumbwheel 330 counter-clockwise until flange 364 returns to the first position. Then, the surgeon pulls upward to release the boss 338 and flange 364 from the apertures 434, 436 of the bone plate 430.

Figure 66:
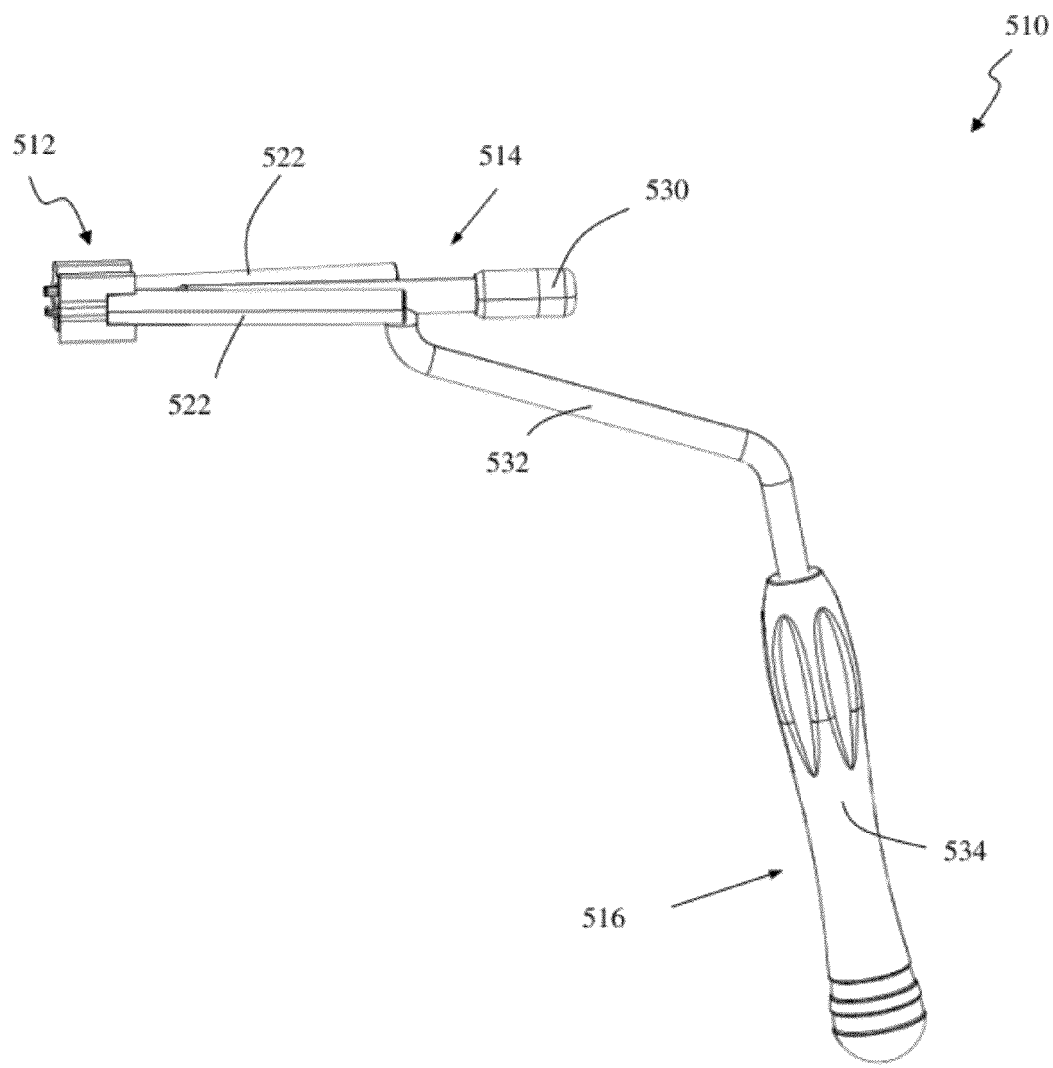
FIG. 66 is a perspective view of an example of a DTS guide according to an alternative embodiment of the present invention.
Figure 67:
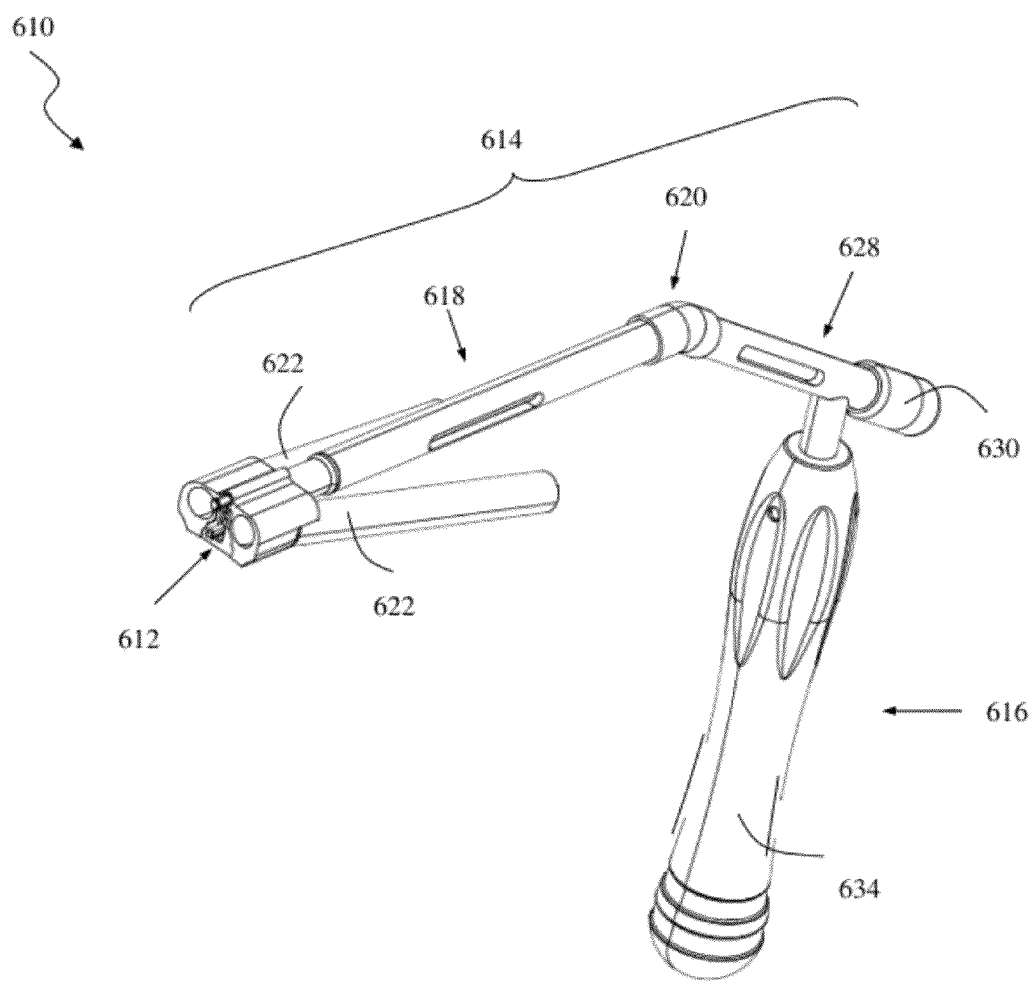
FIG. 67 is a perspective view of an example of a DTS guide according to another alternative embodiment of the present invention.

FIGS. 66-67 illustrate an example of a DTS guide 510 according to a second embodiment of the present invention. The DTS guide 510 functions the same way as the DTS guide 310 and includes substantially the same structure as the DTS guide 310. The DTS guide 510 includes an engagement assembly 512, a body portion 514, and a handle member 516. The DTS guide 510 further includes guide tubes 522, a thumbwheel 530, and a contoured handle 534. Each of these parts is identical in structure and function as the corresponding engagement assembly 312, body portion 314, handle member 316, guide tubes 322, thumbwheel 330 and contoured handle 334 of the DTS guide 310 described above such that a repeat discussion is unnecessary. Structurally, however, the body portion 514 is connected with the contoured handle by an elongated and curved handle shaft 532 such that the contoured handle is offset from the body portion 514 in a longitudinal as well as lateral direction.

An example of a DTS guide 610 according to a third embodiment of the present invention is shown in FIGS. 67-70. The DTS guide 610 is similar to the DTS guide 310 described above, and includes an engagement assembly 612, a body portion 614, and a handle member 616. As with the DTS guide 310, the DTS guide 610 includes a pair of guide tubes 622, a thumbwheel 630, and a contoured handle 634. Each of these parts is identical in structure and function as the corresponding engagement assembly 312, handle member 316, guide tubes 322, thumbwheel 330 and contoured handle 334 of the DTS guide 310 described above such that a repeat discussion is unnecessary. The body portion 614 consists of a first body portion 618, a second body portion 620, and a third body portion 628 which will be described in more detail below. Notably, the first body portion 618 is not axially aligned with the third body portion 628. Rather, the second portion 620 functions to maintain the first body portion 618 in a desired (non linear) angular orientation relative to the third body portion 628.

Figure 68:
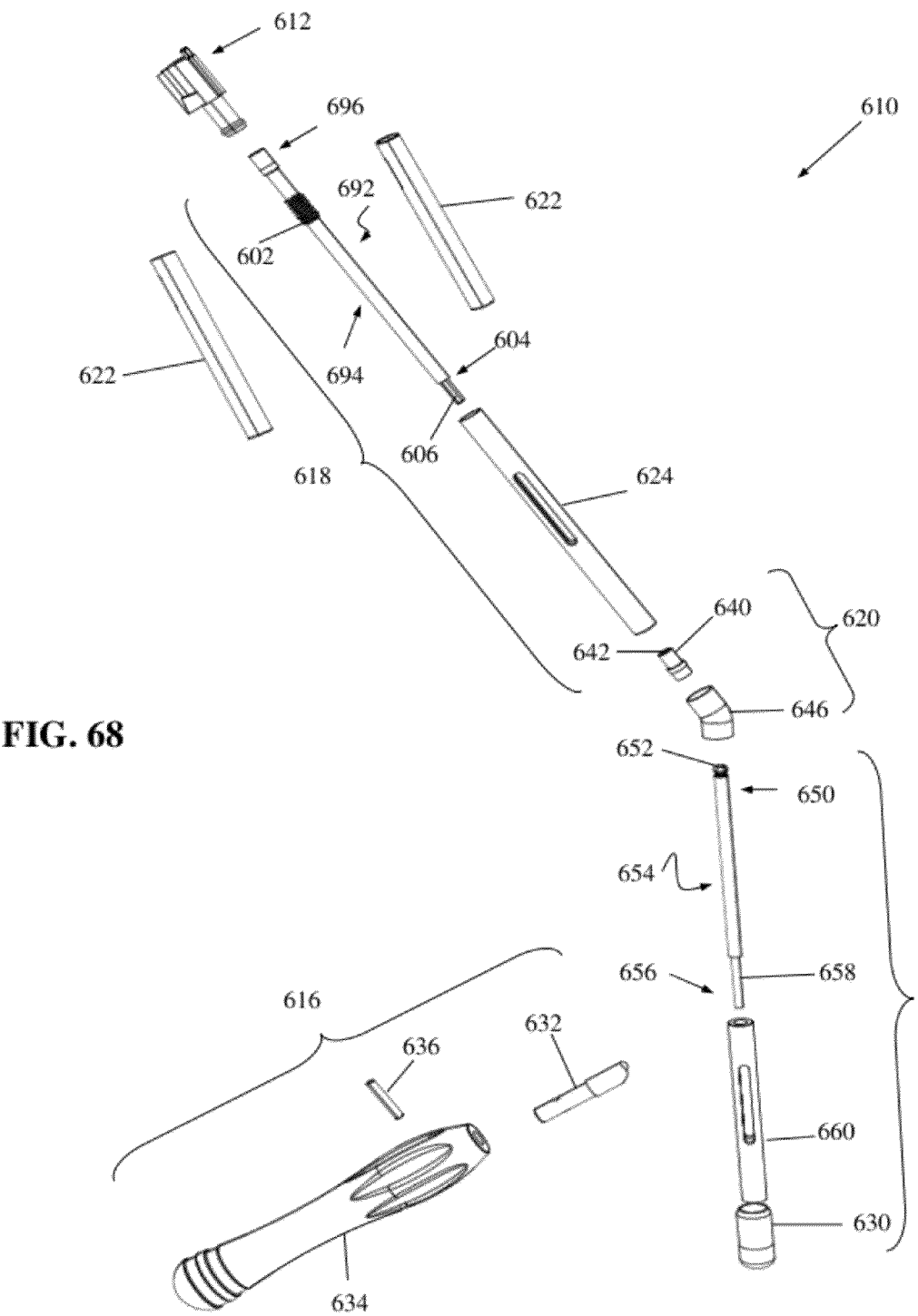
FIG. 68 is an exploded view of the DTS guide of FIG. 67.

Referring to FIG. 68, the first body portion 618 consists of a connector 692 and an outer tube 624. The connector 692 is an elongated generally cylindrical member having a longitudinal axis extending therethrough, and further having a distal end 696, a proximal end 604, and an elongated shaft 694 extending therebetween. Similar to the DTS guide 310 described above, the distal end includes a circular opening for receiving the snap connection from the engagement assembly 612 that is identical in structure and function as the corresponding engagement assembly 312.

The proximal end 604 of connector 692 has a boss 606, extending therefrom that is sized and dimensioned to fit within a first aperture 642 of sleeve 640, as will be described further below. By way of example only, the boss has a hexagonal cross-section; however, other shapes are possible without departing from the scope of the present invention. The elongated shaft 694 has a threaded portion 602 located generally towards the distal end of the elongated shaft 694. Similar to DTS guide 310 described above, the threaded portion 602 of the connector threadedly engages the threaded portion of the outer tube 624 (not shown).

Figure 69:
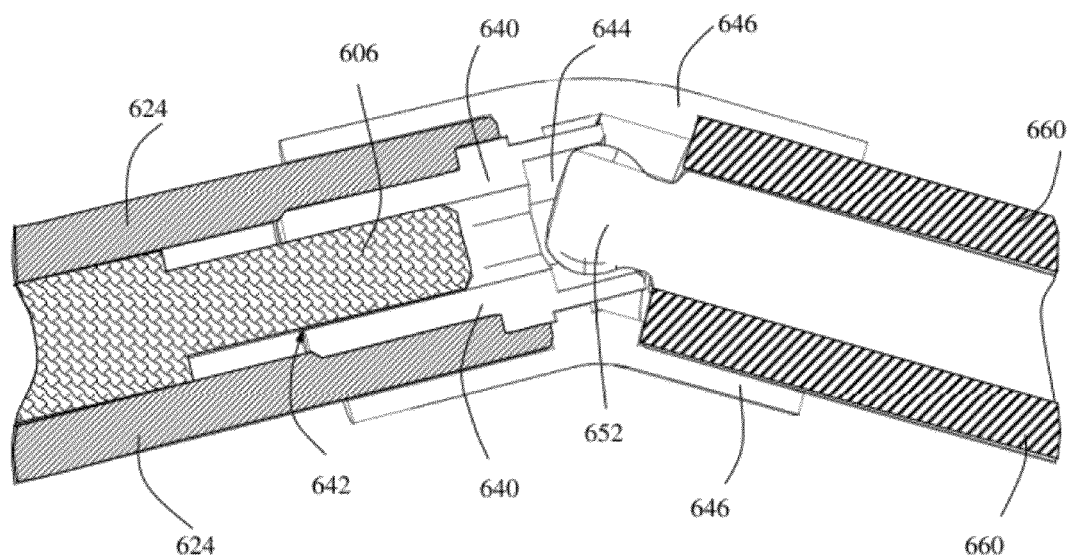
FIG. 69 is a cross-sectional view of a connection region forming part of the DTS guide of FIG. 67.
Figure 70:
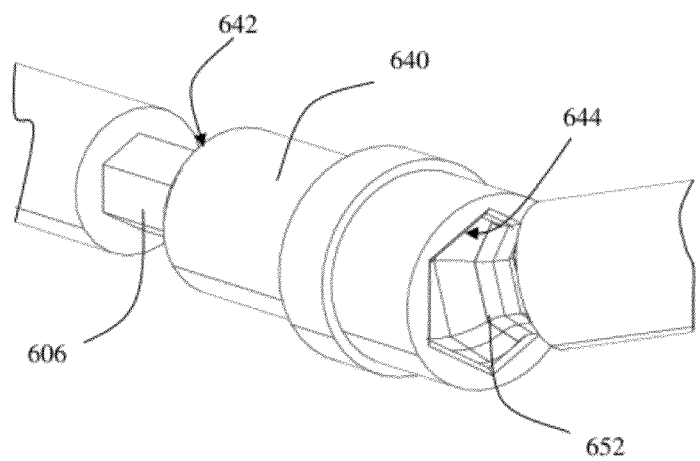
FIG. 70 is an enlarged perspective view of the connection region of FIG. 69.

The second body portion 620 consists of a sleeve 640 and a coupler 646, which are shown in more detail in FIGS. 69 and 70. The sleeve 640 has a first aperture 642, sized and dimensioned, for receiving the boss 606 of connector 692 and a second aperture 644 sized and dimensioned for receiving the ball shaped boss 652 of inner shaft 654. A coupler 646 encloses the sleeve 640 and connects a first outer tube 624 with a second outer tube 660. The coupler 646 functions to maintain the engagement between the ball shaped boss 652 of inner shaft 654 and the second aperture 644 of the sleeve during use. Moreover, the coupler is angled like an elbow joint, functioning to maintain the first body portion 618 in proper angular alignment with the third body portion 628.

The third body portion 628 contains an inner shaft 654 and an outer tube 660. The inner shaft 654 is an elongated, generally cylindrical member having a longitudinal axis extending therethrough and further having a distal end 650, a proximal end 656, and a body portion extending therebetween. The distal end 650 has a ball shaped boss 652 that corresponds to the shape of second aperture 644 of sleeve 640. By way of example only, the ball 652 has a hexagonal cross-section; however other cross-sectional shapes are possible without departing from the scope of the invention. As will be described in further detail below, as the inner shaft 654 rotates, the ball shaped boss 652 creates a torque on the sleeve 640, causing the sleeve 640 to rotate and thereby causing the connector 694 at the other end of sleeve 640 to rotate in the same direction as the inner shaft 654. During this rotation, the connector 692 migrates axially relative to the outer tube 624.

To operate the DTS guide 610, the surgeon rotates the thumbwheel 630 in a clockwise direction. As thumbwheel 630 rotates, the inner shaft 654 will also rotate in the same (clockwise) direction. Due to the interaction between the ball shaped boss 652 with the second aperture 644 of sleeve 640, the boss 606, connected to the first aperture 642 of sleeve 640, will cause connector 692 to also rotate in the same (clockwise) direction. As connector 692 rotates, the interaction between the threaded portion 602 of connector 692 and the threaded portion (not shown) of outer tube 624 causes the connector 692 to migrate distally within outer tube 624. Because the ball shaped boss 652 is engaged with the sleeve 640, the sleeve 640 continues to apply the appropriate torque to turn the connector 692, engaged to the other end of sleeve 640. Finally, connector 692 is connected to the engagement assembly 612 and the engagement assembly functions the same as the corresponding engagement assembly 312 of DTS guide 310 in engaging the DTS guide with a bone plate, as described above.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternative falling within the spirit and scope of the invention as described herein.

What is claimed is:

1. A surgical fixation system for fixing a first bony segment relative to a second bony segment comprising:
   a bone plate sized to span at least two adjacent bony segments, said bone plate including a first plate portion slideably connected to a second plate portion, the first plate portion including a first aperture configured to receive an anchor element, said first aperture positioned on said first plate portion such that the first aperture is situated over said first bony segment when said bone plate is implanted, and the second plate portion including a second aperture configured to receive an anchor element, said second aperture positioned on said second plate portion such that said second aperture is situated over said second bony segment when said bone plate is implanted;
   a plurality of anchor elements configured to anchor said bone plate to said first and second bony segments, each of said anchor elements dimensioned to be received through one of said first and second apertures; and
   a plurality of unbroken annular anti-backout elements disposed within each of said first and second apertures, said anti-backout elements allowing passage of at least a portion of said anchor element therethrough in one direction while resisting passage of at least a portion of said anchor elements therethrough in an opposite direction.

2. The surgical fixation system of claim 1, wherein said anti-backout elements comprised a canted coil ring.

3. The surgical fixation system of claim 1, wherein said anchor element comprises a bone screw.

4. The surgical fixation system of claim 3, wherein said bone screw includes a head region and a threaded shaft region.

5. The surgical fixation system of claim 4, wherein said head region further includes a circumferential recess.

6. The surgical fixation system of claim 5, wherein said bone screw further comprises a washer member disposed within said circumferential recess.

7. The surgical fixation system of claim 6, wherein said washer member comprises an unbroken ring having a generally planar upper surface having a first circumference, a lower surface having a second circumference less than said first circumference, and a generally angled lateral surface extending between said upper and lower surfaces.

8. The surgical fixation system of claim 7, wherein said upper surface is configured to interact with said anti-backout element.

9. The surgical fixation system of claim 6, wherein said recess has a height dimension greater than a height dimension of said washer member.

10. The surgical fixation system of claim 1, further comprising third and fourth apertures configured to receive an anchor element, said third aperture positioned on said first plate portion and adjacent said first aperture such that the third aperture is situated over said first bony segment when said bone plate is implanted, said fourth aperture positioned on said second plate portion and adjacent said second aperture such that the fourth aperture is situated over to said second bony segment when said bone plate is implanted.

11. A systems for fixing a first bone segment to a second bone segment, comprising:

- a bone plate sized to span at least two adjacent bony segments, said bone plate including a first plate portion slideably connected to a second plate portion, the first plate portion including a first fixation aperture configured to receive an anchor element, said first aperture positioned on said first plate portion such that the first aperture is situated over said first bony segment when said bone plate is implanted, and the second plate portion including a second fixation aperture configured to receive an anchor element, said second aperture positioned on said second plate portion such that said second aperture is situated over said second bony segment when said bone plate is implanted;
- a plurality of anchor elements configured to anchor said bone plate to said first and second bony segments, each of said anchor elements dimensioned to be received through one of said first and second apertures;
- a plurality of unbroken annular anti-backout elements disposed within each of said first and second apertures, said anti-backout elements allowing passage of at least a portion of said anchor element therethrough in one direction while resisting passage of at least a portion of said anchor element therethrough in an opposite direction; and
- an inserter configured to releasably engage at least one of the first and second plate portions, the inserter including a first boss configured to engage a first engagement aperture in said plate portion, a pivot member including a flange extending distally from said pivot member, the flange configured to engage a second engagement aperture in said plate portion, an elongated shaft operably connected to said pivot member, wherein rotation of the elongated shaft causes the flange to pivot toward the boss and exert compressive pressure on said plate portion between said boss and flange.

12. The system of claim 11, wherein the inserter further includes a thumbwheel operably connected to the elongated shaft, the thumbwheel configured to be operated by a user.

13. The system of claim 11, wherein the inserter includes at least one guide barrel configured to be aligned with at least one of said first and second fixation apertures.

* * * * *